US011776682B2

(12) United States Patent  
Bossio et al.

(10) Patent No.: US 11,776,682 B2  
(45) Date of Patent: *Oct. 3, 2023

(54) DOSE PREPARATION DATA ANALYTICS

(71) Applicant: BAXTER CORPORATION ENGLEWOOD, Englewood, CO (US)

(72) Inventors: Robert Joseph Bossio, Palm Coast, FL (US); Bhavesh S. Padmani, Port Orange, FL (US); Matthew A. Valentine, Ormond Beach, FL (US)

(73) Assignee: Baxter Corporation Englewood, Englewood, CO (US)

( * ) Notice: Subject to any disclaimer, the term of this patent is extended or adjusted under 35 U.S.C. 154(b) by 422 days.

This patent is subject to a terminal disclaimer.

(21) Appl. No.: 17/076,453

(22) Filed: Oct. 21, 2020

(65) Prior Publication Data

US 2021/0035681 A1  Feb. 4, 2021

Related U.S. Application Data

(62) Division of application No. 14/957,819, filed on Dec. 3, 2015, now Pat. No. 10,818,387.

(Continued)

(51) Int. Cl.  
*G16H 40/20* (2018.01)  
*G16H 15/00* (2018.01)  
(Continued)

(52) U.S. Cl.  
CPC ............. *G16H 40/20* (2018.01); *G16H 15/00* (2018.01); *G16H 20/10* (2018.01); *G16H 70/40* (2018.01)

(58) Field of Classification Search  
CPC ........ G16H 40/20; G16H 40/00; G16H 15/00; G16H 20/10; G16H 20/00; G16H 70/40; G16H 70/00  
See application file for complete search history.

(56) References Cited

U.S. PATENT DOCUMENTS

2002/0010679 A1  1/2002  Felsher  
2005/0021369 A1*  1/2005  Cohen ................... G16H 40/20  
                                                            455/73

(Continued)

FOREIGN PATENT DOCUMENTS

JP        2005284703         10/2005  
WO   WO-2005043440 A1 *  5/2005  ............... B65B 1/30

OTHER PUBLICATIONS

Examination Report for related Australian Application No. 2021215115; report dated Sep. 8, 2022; (6 pages).

(Continued)

*Primary Examiner* — Jason S Tiedeman  
*Assistant Examiner* — Alicia Marie Runser  
(74) *Attorney, Agent, or Firm* — K&L Gates LLP

(57) ABSTRACT

Providing selective, secure access to an aggregated, multidimensional data set comprising dose order records for generation of data analytics with respect thereto. The aggregated data may correspond to a plurality of unaffiliated facilities. As such, upon a user from a given facility attempting to access a data analytics tool may be identified in relation to a facility from which the user is accessing the tool. In turn, a data cube class definition from which all other data analytics data cubes inherit from may be used to, in conjunction with the user identification, limit the data used to generate data analytics outputs to source data to which the user has authorization to view. The outputs may include including, for example, reports, dashboards, tables, or the like.

22 Claims, 11 Drawing Sheets

Related U.S. Application Data

(60) Provisional application No. 62/088,358, filed on Dec. 5, 2014.

(51) Int. Cl.
    *G16H 20/10*     (2018.01)
    *G16H 70/40*     (2018.01)

(56) References Cited

U.S. PATENT DOCUMENTS

| | | |
|---|---|---|
| 2008/0288524 A1 | 11/2008 | Dumitru et al. |
| 2009/0024414 A1 | 1/2009 | Mansour et al. |
| 2009/0216560 A1* | 8/2009 | Siegel .................... G16H 20/10 |
| | | 705/2 |
| 2010/0179831 A1 | 7/2010 | Brown et al. |

OTHER PUBLICATIONS

New Zealand Patent Examination Report dated Sep. 15, 2021—3 pages.
EP Communication re Oral Proceedings—Application No. 15865852.6 1126—2 pages.
EP Communication Decision to refuse EP Patent Application No. 15865852.6—15 pages.

* cited by examiner

DOSE PREPARATION DATA ANALYTICS

CROSS-REFERENCE TO RELATED APPLICATION

The present application is a divisional application of U.S. application Ser. No. 14/957,819, filed on Dec. 3, 2015, now U.S. Pat. No. 10,818,387, entitled "DOSE PREPARATION DATA ANALYTICS", which claims priority to U.S. Provisional Application No. 62/088,358, filed on Dec. 5, 2014, entitled "DOSE PREPARATION DATA ANALYTICS," the contents of which are incorporated by reference herein as if set forth in full.

FIELD

The present disclosure generally relates to the field of healthcare data management and in particular to facilitating data analytics for use with dose order record information such that specific, limited access to a multidimensional repository of data is provided, for example, based on a facility corresponding to a user of the tool and data related to the facility.

BACKGROUND

Healthcare facilities such as hospitals or the like often provide dose order information to a pharmacy in connection with a request to prepare a dose order record for administration to a patient. Traditional approaches to processing the dose orders received at a pharmacy included, for instance, printing physical labels for each dose order to be prepared. In turn, any activity in the pharmacy in relation to the dose orders was premised on the use of the physical labels for workflow management. In addition to the susceptibility for such physical labels to be lost, misplaced, or confused, the ability for pharmacy staff to organize, manage, or communicate the dose orders represented by the physical labels was limited.

In addition to the limitations of traditional approaches in connection with the preparation of dose orders at a pharmacy, the ability to quantify, track, and otherwise review pharmacy activity after preparation of the dose orders was also limited. For instance, the use of physical labels, which would be attached to the dose order upon completion of the preparation, left no means for logging or auditing the activities performed in the pharmacy in relation to specific dose orders absent tedious manual recordation of pharmacy work. Manual recordation of pharmacy work is time consuming, prone to error, and unreliable, and thus does not present a viable option for quantifying, tracking, and reviewing pharmacy activity. In turn, valuable information in relation to the activity of the pharmacy was not visible to pharmacy or hospital management.

Pharmacy workflow management applications have been developed to assist in the preparation, tracking, organization, and documentation of dose orders that are to be prepared or have been prepared by a pharmacy or the like. For example, co-owned U.S. patent application Ser. No. 14/022,415 entitled "MANAGEMENT, REPORTING AND BENCHMARKING OF MEDICATION PREPARATION" filed on Sep. 10, 2013, the entirety of which is incorporated by reference in its entirety. In this regard, dose order records that include received and/or appended dose order information and/or dose order metadata may be generated and stored at a facility that prepares dose orders for administration to a patient. Additionally such dose order records may be stored at a central server that is in operative communication with a plurality of facilities. In this regard, dose order records from a plurality of facilities may be collectively stored at the central server (e.g., for purposes related to data back up or the like).

SUMMARY

In view of the foregoing, it has been recognized that dose order information from a plurality of facilities that is stored at a central location (e.g., a central server) may be advantageously utilized to provide reporting, metrics, or the like with respect to the stored data related to one or more facilities. Specifically, a data analytics tool may be provided that is in operative communication with the central server that may access the data stored at the central server to provide data analytics (e.g., dynamic reports or the like). As the data analytics tool may access the data at the central server, such analytics may be provided in relation to one or more facilities without each individual facility having to maintain an interface to the data analytics tool. However, as the data at the central server may include data from a plurality of different facilities, it has also been recognized that providing selective access to such report may advantageously allow for centralized application of a data analytics tool while maintaining security and restricted access to individuals from respective ones of the facilities when accessing data at the central server.

As such, the present disclosure describes healthcare data management that provides the ability to provide data analytics tools for use in relation to multidimensional data regarding dose order records. Specifically, the present disclosure contemplates allowing selective access to a multidimensional data set. For instance, dose order records from a plurality of facilities may be collectively stored as a multidimensional data set. A base data cube class definition may be generated that uses an identification of a user accessing the tool to determine a subset of the records to which the user has access. In this regard, the base cube class definition may have a data dimension that allows the filtering of data records for presentation to a user in a dynamically generated report. In this regard, additional data cube class definitions may inherit from the base data cube class definition so that a user may only retrieve report data corresponding to data to which they are authorized for access.

In this regard, a first aspect includes a method for providing a user selective access to a data analytics tool for processing a multidimensional data set corresponding to dose order records for use in providing data analytics to the user regarding a subset of the dose order records of the multidimensional data set. The method includes storing a multidimensional data set comprising information corresponding to a plurality of dose order records. The plurality of dose order records of the multidimensional data set comprises at least one indication of a facility corresponding to the dose order records. The multidimensional data set comprises dose order records corresponding to a plurality of facilities. The method further includes receiving user information from a user at one of the plurality of facilities. The user information is indicative of a given facility from which the user is accessing a data analytics tool. The method also includes providing the data analytics tool access to the multidimensional data set to generate a dynamically generated report regarding a subset of the multidimensional data set corresponding to the given facility from which the user is accessing the data analytics tool. Additionally, the method includes presenting to the user at a user interface the dynamically generated report regarding the subset of the multidimensional data set corresponding to the given facility from which the user is accessing the data analytics tool.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For instance, in an embodiment the data analytics tool may include a plurality of data cube class definitions applicable to the multidimensional data set to generate the dynamically generated report. The plurality of data cube class definitions may include a base cube class definition from which all others of the plurality of data cube class definitions depend. The base cube class definition may include at least one data dimension related to the at least one indication of a facility corresponding to the dose order records. In turn, the method may include applying the base cube class definition to the multidimensional data set based on the user information indicative of a given facility from which the user is accessing the data analytics tool and building a data cube based on the applying that limits the data accessible by the user to the subset of the multidimensional data set corresponding to the given facility from which the user is accessing the data analytics tool.

In an embodiment, the building may include performing at least one data transformation operation on the subset of the multidimensional data set, wherein the at least one data transformation operation is defined in the base cube class definition. The at least one data transformation may include automatically transcribing a first data field for each given dose order record in the subset with a second data field of the respective ones of the dose order records of the subset. The at least one data transformation may be applied only to a given type of dose order records. The type of dose order records may be total parenteral nutrition (TPN) doses, the first data field may be a dose description field, and the second field may be a drug name field for the given dose.

In an embodiment, the method may further include invoking another of the data cube class definitions depending from the base cube class definition for application to the subset of the multidimensional data set corresponding to the given facility from which the user is accessing the data analytics tool to generate the dynamically generated report regarding the subset of the multidimensional data set. In certain applications, the plurality of data cube class definitions may include a parameter indicative of whether data cubes built using the data cube class definitions include protected health information (PHI). The parameter may be dynamically generated based on at least one dimension of the data cube class definition.

In an embodiment, the receiving may include receiving login information at a local server resident at the facility from which the user is accessing the data analytics tool to initiate a user session, authenticating the user to a central server based on the login information received at the local server, and populating a session variable related to the user session based on authenticated user login information. The session variable may include the user information indicative of the given facility from which the user is accessing the data analytics tool. In this regard, the method may include a delegated authentication process that may, in at least some applications, include passing a token at least partially based on the session variable to the data analytics tool. The token may be compared to available tokens at the central server to determine if the user is to be granted access to the data analytics tool. Accordingly, upon matching the token to one of the available tokens, the token may be issued to the user and the corresponding available token is removed from the central server. In some applications, the session variable includes a role definition for the user generated based at least in part on the login information received by the user. The role definition may include indications as to the ability of the user in relation to viewing reports, editing reports, viewing cube class definitions, editing cube class definitions, viewing pivot tables, editing pivot tables, viewing dashboards, and editing dashboards.

The method may further include logging user activity in relation to the use of the data analytics tool by the user. The logging may include recording information regarding the user and the usage of the data analytics tool by the user. The logging may include recording the identity of the dynamically generated report presented to the user. The logging may include recording whether the dynamically generated report presented to the user contained protected health information (PHI). The multidimensional data set may include data regarding the identity of doses, data regarding the steps of preparing the doses, data regarding the timing of doses, data regarding errors that occurred during dose preparation, data regarding product waste, data regarding drug usage, data regarding drug therapies administered, and data regarding drug interactions.

A second aspect includes a system for implementation of a data analytics tool for processing a multidimensional data set corresponding to dose order records for data analytics regarding a subset of the dose order records of the multidimensional data set. The system includes a central server that is in operative communication with a plurality of local servers, each of the local servers being disposed at a corresponding respective facility that prepares doses corresponding to dose orders for administration to a patient. The central server receives information regarding dose order records corresponding to the dose orders from the local servers. The system also includes a database at the central server that stores a data structure comprising a multidimensional data set including a plurality of dose order records received from the plurality of local servers. Each of the plurality of dose order records of the multidimensional data set comprises at least one indication of the facility from which the dose order record was received. The system may also include a local server interface in operative communication with the plurality of local servers for receiving from at least one of the plurality of local servers user information from a user at one of the plurality of facilities. The user information is indicative of a given facility from which the user is accessing a data analytics tool. The system also includes a data analytics interface that facilitates operative communication with a data analytics tool. The data analytics interface provides a data analytics tool access to the multidimensional data set stored in the database to generate a dynamically generated report regarding a subset of the multidimensional data set corresponding to the given facility from which the user is accessing the data analytics tool based on the user information received from the local server interface. The system also includes a user interface for presenting to the user at a user interface the dynamically generated report regarding the subset of the multidimensional data set corresponding to the given facility from which the user is accessing the data analytics tool.

A number of feature refinements and additional features are applicable to the second aspect. These feature refinements and additional features may be used individually or in any combination. As such, each of the features discussed above in connection with the first aspect may be, but are not required to be, used with any other feature or combination of features of the second aspect.

A third aspect includes a system for providing a user selective access to a data analytics tool for processing a multidimensional data set corresponding to dose order records for use in providing data analytics to the user regarding a subset of the dose order records of the multidimensional data set. The system includes a central server that is in operative communication with a plurality of local servers, each of the local servers being disposed at a corresponding respective facility that prepares doses corresponding to dose orders for administration to a patient. The central server receives information regarding dose order records corresponding to the dose orders from the local servers. The system also includes a database at the central server that stores a data structure comprising a multidimensional data set including a plurality of dose order records received from the plurality of local servers. Each of the plurality of dose order records of the multidimensional data set comprises at least one indication of the facility from which the dose order record was received. The system also includes a local server interface in operative communication with the plurality of local servers for receiving from at least one of the plurality of local servers user information from a user at one of the plurality of facilities. The user information is indicative of a given facility from which the user is accessing a data analytics tool. The system also includes a data analytics tool in operative communication with the database for access to the multidimensional data set stored in the database to generate a dynamically generated report regarding a subset of the multidimensional data set corresponding to the given facility from which the user is accessing the data analytics tool based on the user information received from the local server interface. The system also includes a user interface for presenting to the user at a user interface the dynamically generated report regarding the subset of the multidimensional data set corresponding to the given facility from which the user is accessing the data analytics tool.

A number of feature refinements and additional features are applicable to the third aspect. These feature refinements and additional features may be used individually or in any combination. As such, each of the features discussed above in relation to the first aspect may be, but are not required to be, used with any other feature or combination of features of the third aspect.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

Figure 1:
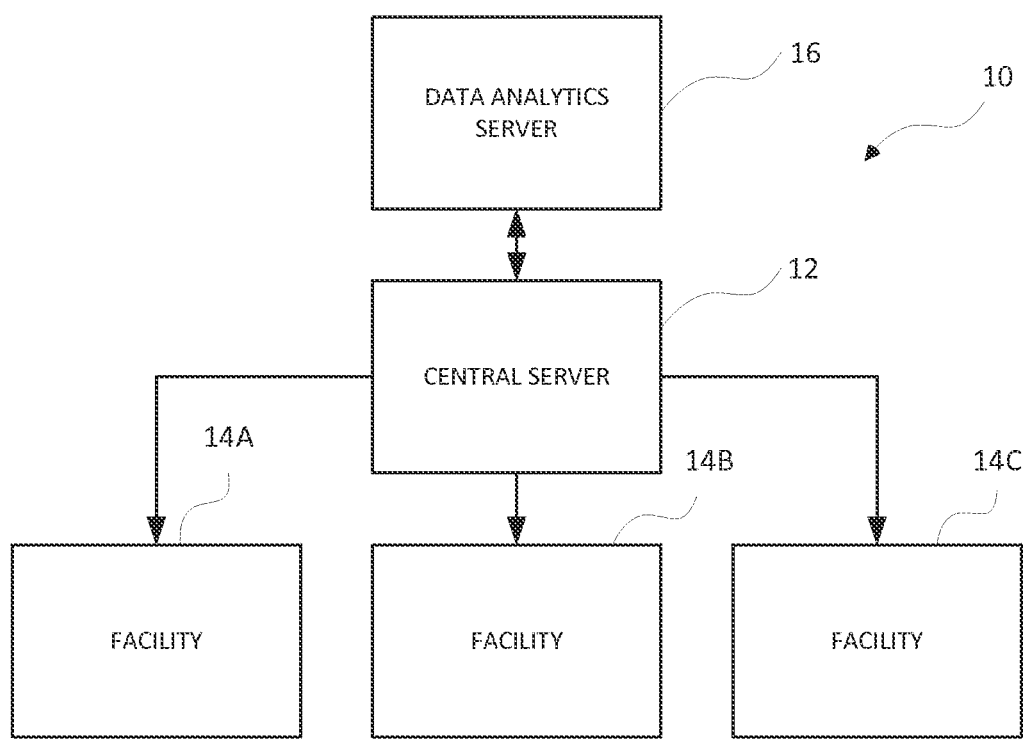
FIG. 1 is a schematic view of an embodiment of a system for selective, secure data analytics in relation to an aggregated multidimensional data set from a plurality of facilities.

With reference to FIG. 1, a system 10 that facilitates selective, secure data analytics in a distributed environment as described herein is depicted. The system 10 may include a central server 12. The central server 12 may be in operative communication with a plurality of facilities 14. For instance, as shown in FIG. 1, the central server 12 may be in operative communication with a first facility 14A, a second facility 14B, and a third facility 14C. While three facilities 14A, 14B, and 14C are shown in FIG. 1 for purposes of illustration, it will be understood that fewer or additional facilities 14 may be provided in operative communication with the central server 12 and the three facilities 14A-14C depicted in FIG. 1 are for illustrative purposes only.

Accordingly, in at least one embodiment, the facilities 14 may comprise unaffiliated and discrete healthcare facilities 14 capable of preparing medication doses for administration to patients. The central server 12 may be hosted by another discrete and unaffiliated third-party that may be separate from any of entities of the facilities 14. For instance, the central server 12 may be hosted and/or executed by an application provider that provides one or more client applications for execution by the facilities 14 to facilitate a pharmacy workflow management application. Specifically, the central server 12 may be executed or hosted by an application provider that provides the pharmacy workflow management application each facility 14.

As such, the facilities 14A, 14B, and 14C may execute a pharmacy workflow management application that may allow for the facilities 14A, 14B, and 14C to receive, process, organize, prepare, track, or otherwise manage dose orders to be prepared at each of the respective facilities 14A, 14B, or 14C. In this regard, each facility 14 may generate dose order information related to dose orders processed at each respective one of the facilities 14. In turn, facilities 14 may be in operative communication with the central server 12 and may provide dose order data to the central server 12.

In this regard, dose order data may include any one or more classes of information regarding dose orders processed. For instance, the dose order data may include information corresponding with the dose order received at the pharmacy (e.g., including information entered by way of a physician order entry (POE) system, received by a pharmacy information system (PhIS), or the like). The dose order data may also include data appended to and/or generated in connection with the preparation of a dose order. This information may include data related to the products (e.g., drug products, pharmacy products, or hardware) used to prepare the dose order. As such, the information may include information regarding one or more drugs (or all drugs) used to prepare the dose such as a national drug code (NDC), a lot number, and expiration, etc. The information may also include preparation metadata such as information related to the identity of personnel taking action with respect to a dose, time events related to a dose, images associated with dose preparation and/or verification, errors that were detected or occurred during dose processing, information related to a pharmacist review of a dose, tracking information regarding a dose in the pharmacy and/or administration environment, etc. In short, the dose order data may comprise any information regarding the dose order or preparation of the dose order that is recorded, generated, appended, or otherwise associated with the dose order.

Additionally, a data analytics server 16 may be operative communication with the central server 12. As will be discussed in greater detail below, the data analytics server 16 may comprise a data analytics tools that may be applied to data at the central server 12 to generate, for example, dynamically generated reports for use in data analytics with respect to the data to which the data analytics tool is applied at the central server 12. The data analytics tool may include data cube class definitions that define data organization and transactions carried out with respect to data to facilitate generation of dynamic reports for use in data analytics. Such data cube class definitions are described in greater detail below. In any regard, it may be appreciated that the data cube class definitions may be applied to data at the central server 12 to facilitate data analytics with respect to the data to which the data cube class definitions provided by the data analytics tool as applied.

As such, users from each respective facility 14 may be operative to access the data analytics tool provided by the analytics server 16 to invoke the data analytics tool for use in connection with data stored on the central server 12. As outlined briefly above, while provision of the data analytics server 16 in operative communication with the central server 12 may simplify the interface complexity of the system 10 (e.g., in contrast providing a data analytics server connection directly to each facility), the interface with a central server 12 may result in the need to provide selective, secure access to the data stored in the central server 12. Specifically, as the central server 12 may store data from a plurality of facilities 14, it may be that users from a given facility (e.g., the first facility 14A) should not be provided access to data from other facilities (e.g., the second facility 14B or third facility 14C). That is, selective access to users may be provided such that users of a given facility may only be provided access to data analytics with respect to data for the facility from which the user is accessing the data analytics tool. In this regard, the system 10, as described in greater detail below, may provide selective, secure access to a data analytics tool with respect to a portion of data specific to the facility 14 from which the data analytics tool is accessed.

While the following disclosure mentions providing selective access on a facility by facility basis by determining a facility from which a user is accessing the data analytics tool, it may be appreciated that a user accessing the tool from a given facility may be an organizational user. That is, a plurality of facilities may comprise an organization. As such, a user accessing the tool from a given one of the facilities comprising the organization may have credentials sufficient access data from the plurality of facilities comprising the organization. Thus while potentially referenced herein as a facility by facility determination of access to data, the system may be executed such that any data at the central server may be analyzed using the data analytics tool so long as a user accessing the tool has sufficient credentials to view the data and utilize the tool.

Figure 2:
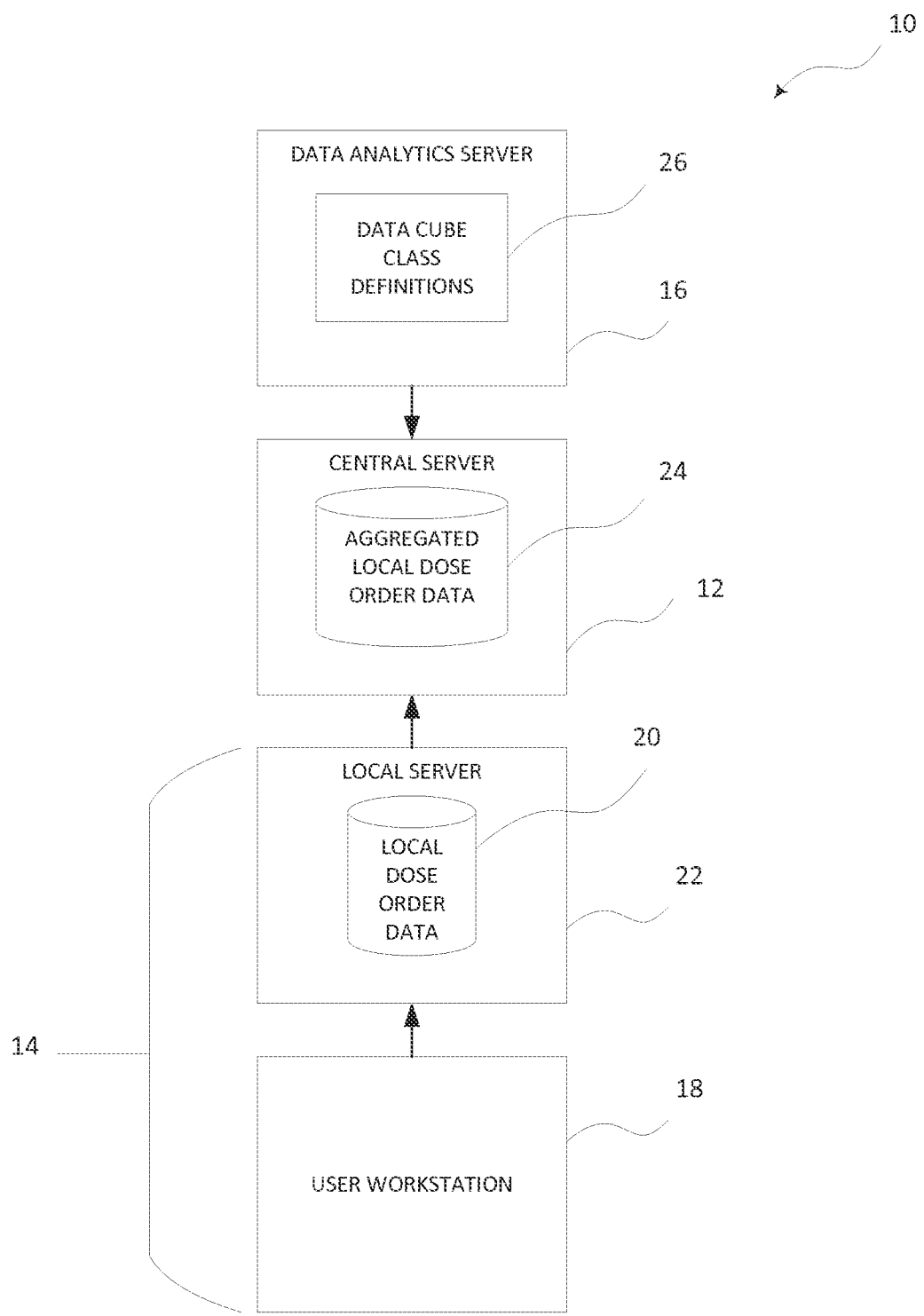
FIG. 2 is a schematic view of an embodiment of a data flow in relation to an example facility relative to the system of FIG. 1.

FIG. 2 further depicts a schematic view of the system 10 that illustrates information flow between portions of the system 10. In FIG. 2, a user workstation 18 and local server 22 may be provided at each instance of a facility 14. While a single instance of the facility 14 is depicted in FIG. 2, it may be appreciated that, in connection with the disclosure of FIG. 1, a plurality of facilities 14 each having a user workstation 18 and local server may undergo a similar information flow is that described with respect to the given facility 14 depicted in FIG. 2. Furthermore, while single user workstation 18 is depicted in operative communication with the local server 20, it may be appreciated that a plurality of user workstations 18 may be provided in operative communication with the local server 20 and may generally follow the description provided herein. The user workstation 18 may be in operative communication with the local server 20 and may exchange dose order data between the user workstation 18 the local server 20. This data exchange may include exchange of dose order information between a local dose order data repository 22 (e.g., stored in a database or the like at the local server 20) and the user workstation 18. This may facilitate provision of dose order information to the user workstation 18 for use in preparation of doses, generation or capture of dose order information, review of prepared dose orders by a pharmacist, or other activities provided by a pharmacy workflow manager.

The local dose order data 22 may be provided from the local server 20 to the central server 12. In this regard, the central server 12 may store aggregated local dose order data 24. For instance, the aggregated local dose order data 24 may include dose order data received a plurality of facilities as illustrated in FIG. 1. As may be appreciated, the dose order data at the aggregated local dose order data 24 may include an indicator as to the facility (or organization) from which the data 24 was received. In turn, the data analytics server 16 may include data cube class definitions 26. As described in greater detail below, the data cube class definitions 26 may define values, measures, calculated measures, indexes, or other data operations performed on data at the central server 12 to facilitate data analytics in connection with the data analytics tool provided by the data analytics server 16. In this regard, the data cube class definitions 26 may be invoked with respect to data, or a subset of data, provided in the aggregated local dose order data repository 24 located central server 12.

As described above, it is been recognized that the provision of a data analytics tool relative to aggregated data at the central server 12 may provide attendant efficiencies in that a single interface with respect to the central server 12 may be maintained such that interfaces between each given facility 14 and a data analytics server 16 need not be provided or maintained. As such and for example, development of new data cube class definitions 26 may be provided to all users of the data cube without having to specifically develop such cubes for use by each facility 14 individually. However, in connection with performing data analytics on the aggregated local dose order data repository 24, it may be necessary to provide a mechanism that allows for users from respective ones of the facility to access only data at the central server 12 to which the user has corresponding credentials to view. Otherwise, data integrity with respect to each individual one of the facilities 14 may be lost.

Figure 3:
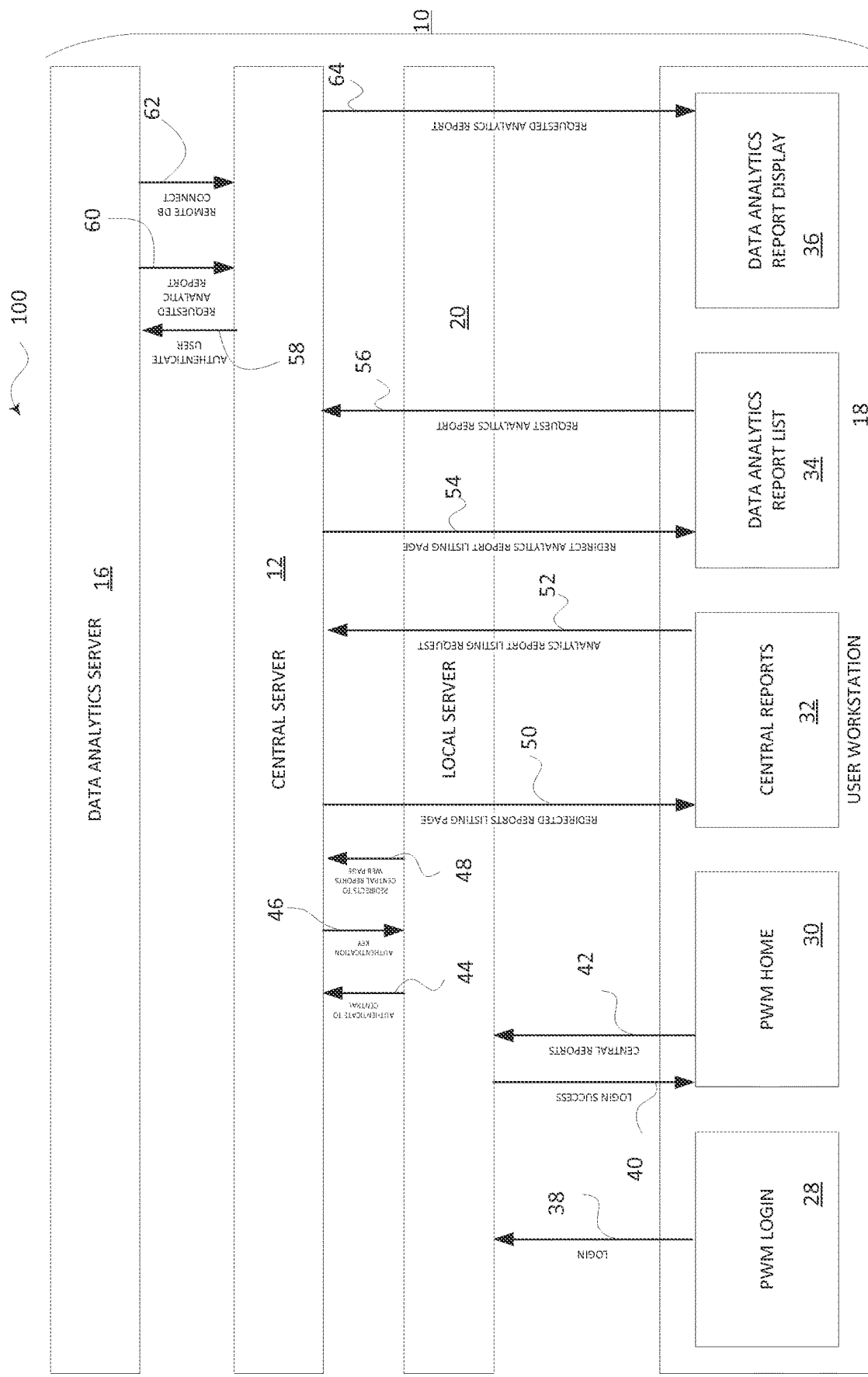
FIG. 3 is a schematic depiction of an embodiment of operation of a system for selective, secure data analytics.

Accordingly, as contemplated herein, a user authentication process may be provided whereby a user may be required to provide user information that may in turn be used to determine a facility from which the user is accessing data analytics tool. Based upon the user identification information, the determination of the data to which the user has access may be appropriately limited to data corresponding to the facility (or organization) corresponding to the user. Accordingly, FIG. 3 depicts a schematic view of a process flow 100 depicted in relation to the system 10 which allows for a user to be authenticated in connection with access to a data analytics tool provided by the data analytics server 16. The authentication of the user may also provide user identification information that may be utilized to determine what data to which the user has access at the central server 12 for use in connection with the data analytics tool. In this regard, the process flow 100 may be utilized to appropriately limit the data to which a user has access to at the central server 12 in connection with the data analytics tool provided by the data analytics server 16. The authentication process may be referred to as a delegated authentication process (as described in greater detail below) as some of the authentication of a user may be performed at a local server 22 and/or central server 12 remote from the data analytics server 16. As such, traditional data analytics tools may require direct access there to for operation on a single data source. However, in the presently described concepts, the data source may, in fact, comprise a plurality of aggregated data sources stored remotely from the data analytics server. As such, the delegated authentication process may allow for access to the remote data in a way such that appropriate data is provided with limited access to appropriate users.

Initially, with respect to FIG. 3, various user interface states associated with user workstation 18 are referenced in relation to the user workstation 18. Accordingly, as may be appreciated by those skilled in the art, the user interface states may correspond to web pages, user interface screens, or other resources accessed by way of a network connection (e.g., including a local area network or wide area network connection). In this regard, the user workstation 18 may be in operative communication with the local server 20, central server 12, and/or data analytics server 16 by way of one or more network connections. In turn, web resources such as web pages or other tools may be accessed at the user workstation 18 to provide the user interface states referenced in FIG. 3. In any regard, the user interface states referenced in FIG. 3 may be rendered at the user workstation 18 in order to allow user to interact with the system 10 is described in greater detail below. As such, the user workstation 18 may, in at least certain embodiments, comprise a thin client that functions to provide functionality provided by a remote access by way the user workstation 18.

Figure 5:
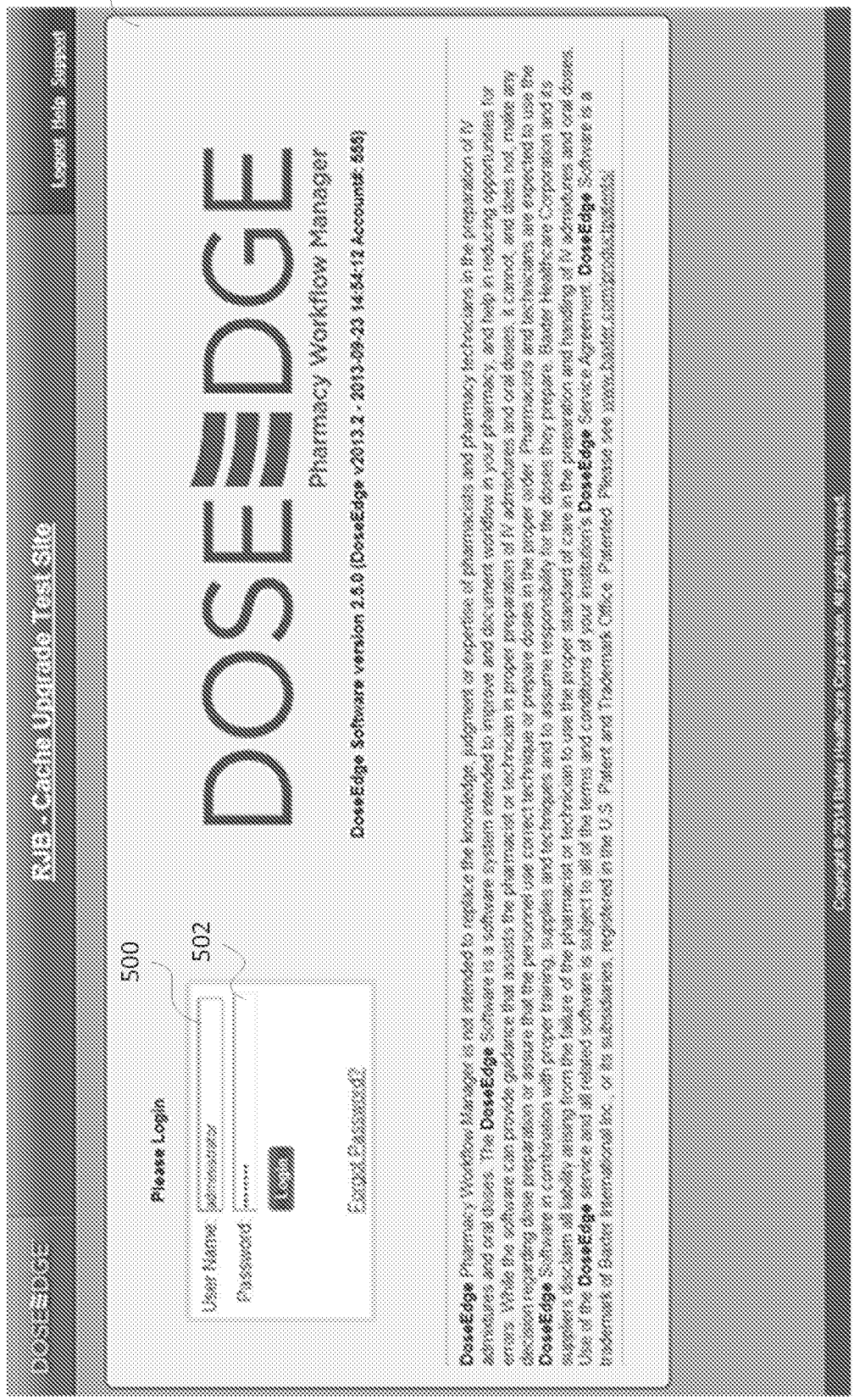
FIG. 5 is a screen shot of an embodiment of a pharmacy workflow management login screen.

The user workstation 18 may initially display a pharmacy workflow management login screen 28. One such example of a pharmacy workflow management login screen 28 is depicted in FIG. 5. In this regard, a user name field 500 and password field 502 may provided on the log in screen 28 presented at the user workstation 18. In turn, a user may enter a username into the user name field 500 and a password into the password field 502. For example, each user at a facility 14 may be assigned a unique username password combination the service identify the user accessing the system 10. As such, the local server 20 may include a record of authorized username password combinations to provide authenticated access to a user attempting to access the system 10.

Accordingly, the user name and password combination entered into the user name field 500 and password field 502 may comprise user authentication information. The provided user authentication information 38 may be communicated to the local server 20. In turn, the local server 20 may process the provided user authentication information (e.g., in reference to the record of authorized username password combinations) to determine whether the user attempting to access the system 10 is authorized to do so. If the user is so authorized (e.g., the user name and password combination provided matches an authorized username password combination stored in the repository the local server 20), the local server 20 may initiate a response 40 that comprises information related to a pharmacy workflow home screen 30. The response 40 may provided to the user workstation 18 such that the pharmacy workflow home screen 30 is displayed to you user workstation 18.

Figure 6:
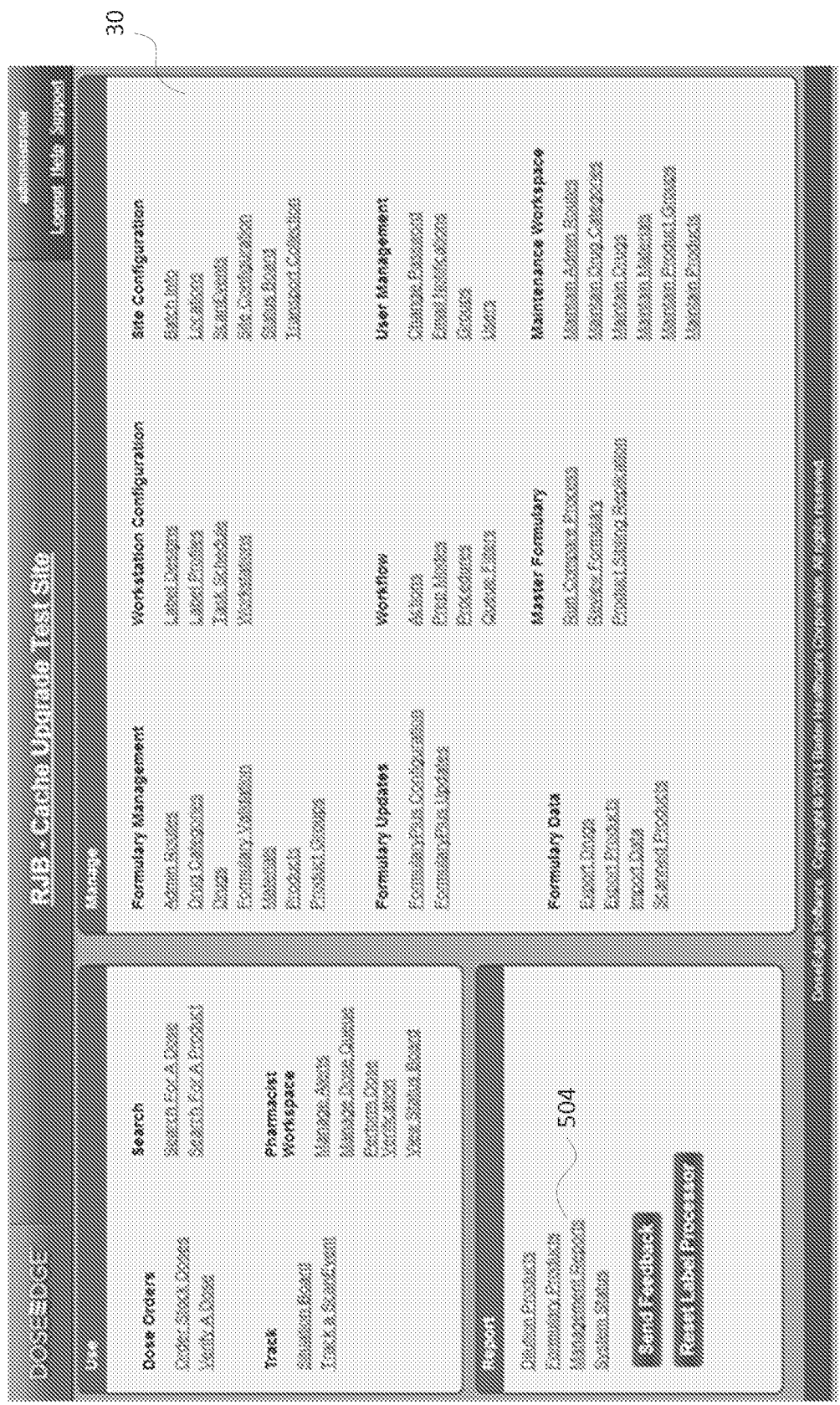
FIG. 6 is a screen shot of an embodiment of a pharmacy workflow management home screen.

With further reference to FIG. 6, an example of a pharmacy workflow manager home screen 30 is depicted. As may be appreciated, the pharmacy workflow manager home screen 30 may include a plurality of links with respect to functionality provided by the pharmacy workflow manager resident at the local server 20. Of interest in the present discussion, the pharmacy workflow manager home screen 30 may include a link 504 that is utilized access the management reports resource provided by the central server 12. In turn, in the event the user wishes to access management reports, the user may click on the management reports link 504. In turn, a request 42 may be provided to the local server 20 requesting access to the management reports resource provided by the central server 12. In turn, the local server 20 may provide to the central server 12 authentication information 44 corresponding with the user requesting access to the management reports. The authentication information 44 may be analyzed at the central server 12 to authenticate the user (e.g., based on the user name and password information provided during the login 38, other information provided by the local server 20, user credential information management the central server 12, and/or other appropriate information).

Figure 7:
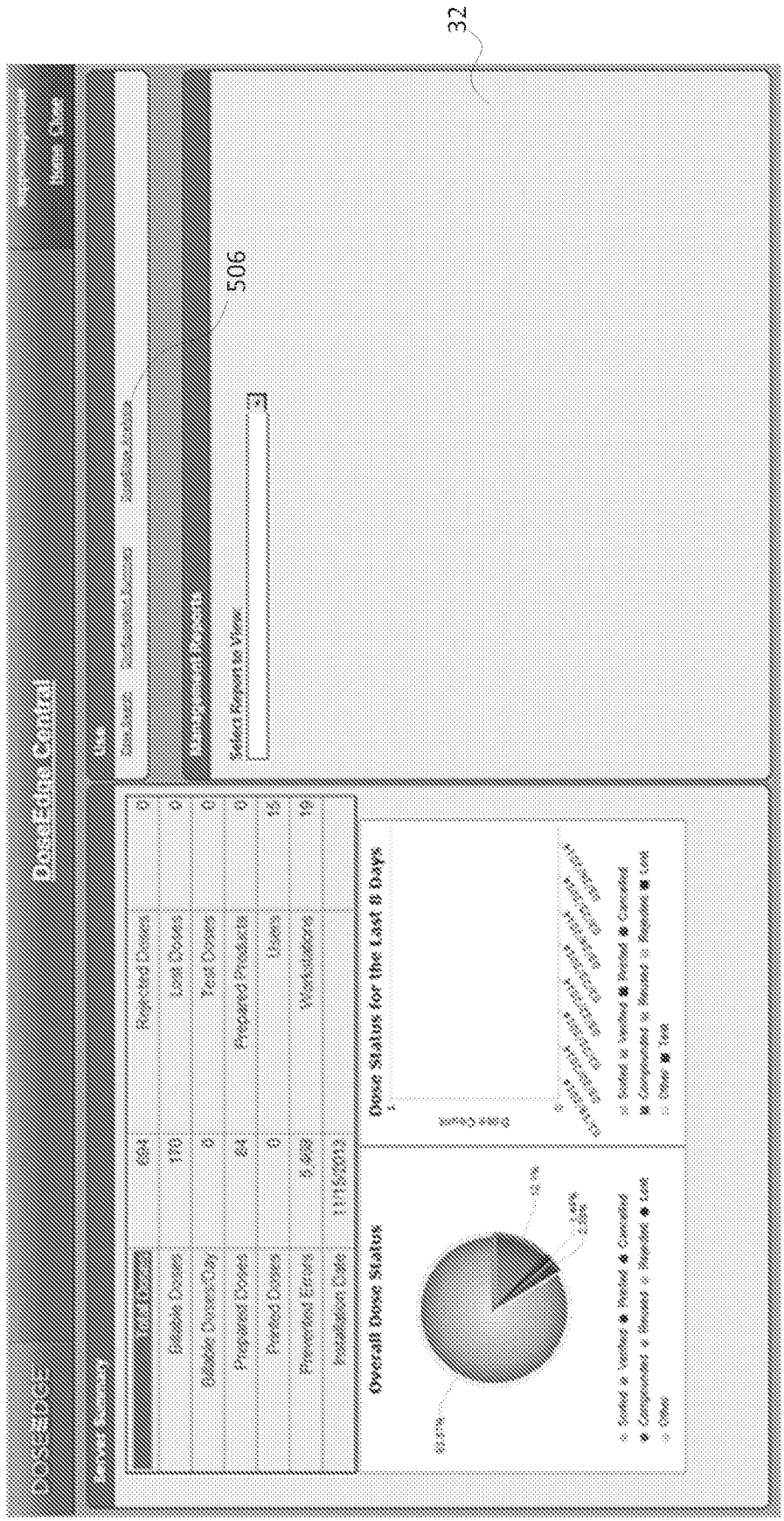
FIG. 7 is a screen shot of an embodiment of a pharmacy central reports screen.

Accordingly, the central server may utilize the authentication information 44 to authenticate the user is having appropriate permissions to access the management reports tool at the central server 12. In turn, the central server 12 may return an authentication key 46 to the local server 20. The local server 20 may in turn provide a redirect command 48 to the central server 12. Upon receipt of the redirect command 48 at the central server 12, the central server 12 may provide a redirection command 50 to the user workstation 18 that redirects the user workstation 18 to a central report screen 32 provided by the central server 12. An example of the central report screen 32 is depicted in FIG. 7. The central report screen 32 may provide static reports regarding the facility from which the user is accessing the central report screen 32. In this regard, the reports provided by the central port screen 32 may not be dynamic and/or provide data analytics tools otherwise provided by the data analytics server 16 as will be described in greater detail below. Thus, as may be appreciated the central reports screen 32 may be provided directly from the central server 12 once the local user is authenticated to the central server 12.

Figure 8:
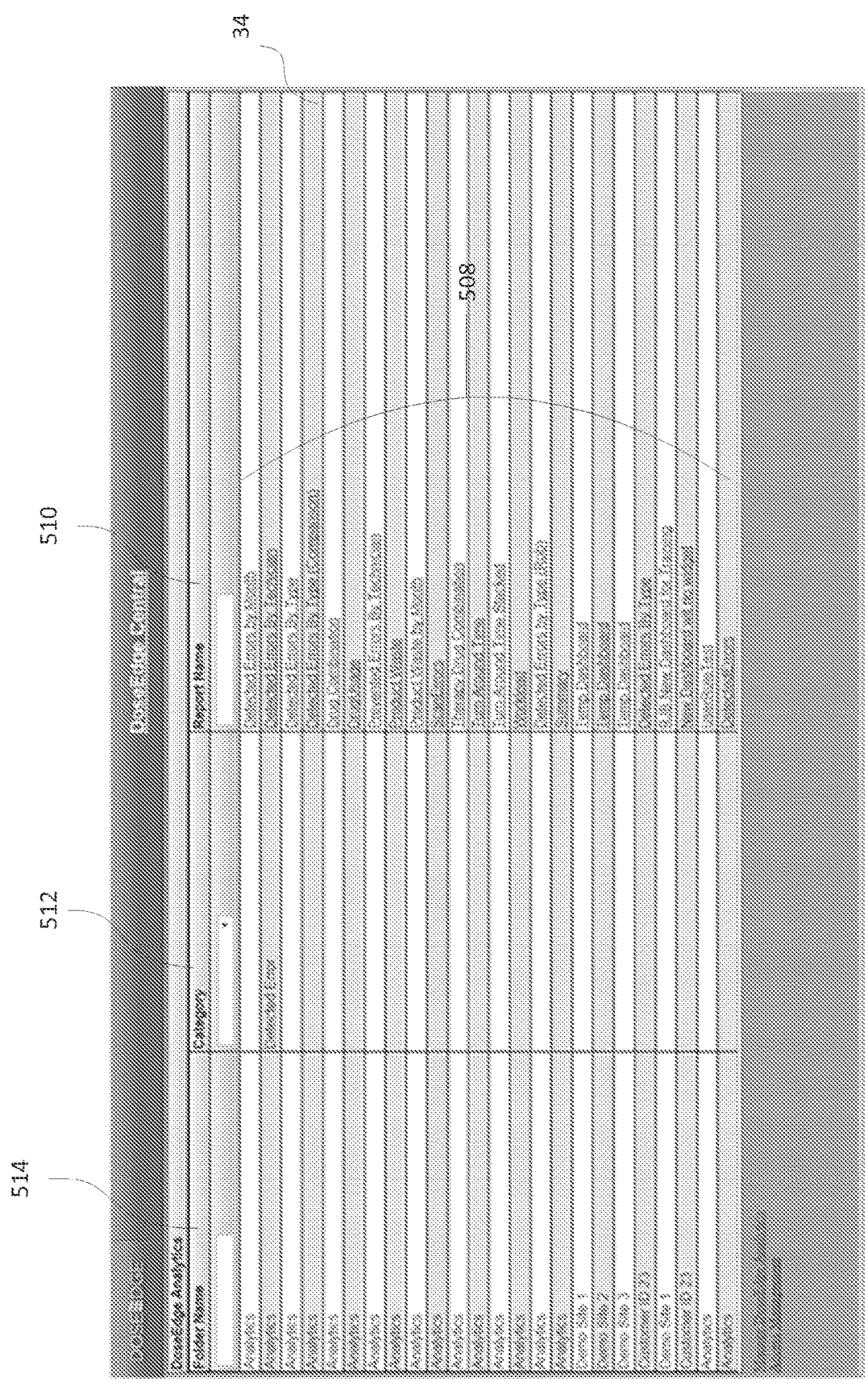
FIG. 8 is a screen shot of an embodiment of a data analytics report list screen.

Additionally, if access the data analytics server 16 is authorized for the given user accessing the central report screen 32, a link 506 to the analytics tool may be provided. The link 506 at the central reports screen 32 may be selected to generate a request 52 for access to an analytics report listing page. In this regard, upon selection of the link 506, the request 52 may be provided to the central server 12 requesting the analytics report listing from the central server 12. In turn, the central server 12 may redirect the user to the data analytics report list screen 34 by providing a redirect command 54 to the user workstation 18. An example of a data analytics report listing screen 34 is provided in FIG. 8. The data analytics report list screen 34 may include a plurality of links 508 to different reports that may be furnished by the data analytics server 16. For instance, different reports 508 may each be furnished by a different data cube class definition as will be discussed in greater detail below.

The data analytics report listing screen 34 may provide the reports 508 in an organized fashion. In this regard, the links 508 to the reports may be provided in a report listing 510. The report listing 510 may include categories 512 that may be arranged in folders 514 for organization of the report links 508. A folder 514 may be generated that may be specific to a given facility and/or given user. In this regard, with the appropriate responsibility or role, a user may be operative to save a copy of a data cube and/or a report generated based on a data cube into the user or facility specific folder. In this regard, a user may be operative to modify the resulting report as desired when saving to the folder. The modifiable report may be saved in a nonpublic folder for access by only that given user or users from a particular facility. Upon selection of a link to report name 508, a request 56 may be provided to the central server 12 requesting the report.

Figure 9:
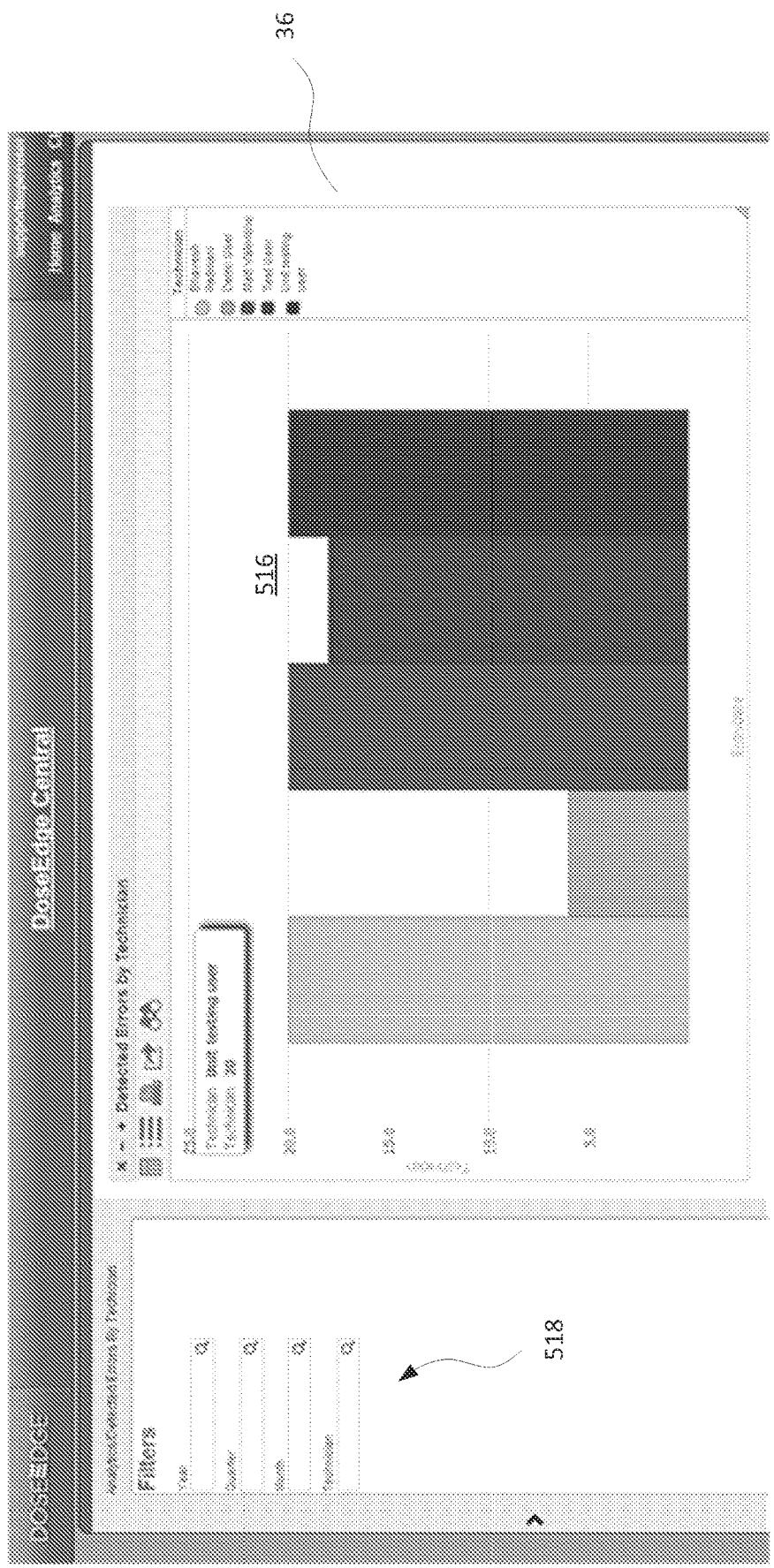
FIG. 9 is a screen shot of an embodiment of a data analytics report display screen.

Upon receipt of the request 56 for a selected report 508, the central server 12 may provide authentication information 58 to the data analytics server 16 to authenticate the user. For instance, the authentication information 58 may comprise or be at least partially based upon user information provided login 38. Upon authentication of the user to the data analytics server 16, a data cube class definition corresponding to the selected report may be invoked and applied to data at the central server 12. In this regard, the requested analytic report may have a corresponding data cube class definition is maintained at the data analytics server 16 that may be provided to furnish the requested analytic report. In this regard, the data cube class definition may be provided 60 to the central server 12 for application to data maintained at the central server 12 to facilitate provision of the requested analytics report by a communication 64 of the report to a data analytics report display screen 36. One such example of the data analytics report display webpage 36 shown in FIG. 9.

The data analytics report display screen 36 may be populated with the requested data analytics report 64 return to the user workstation 18. In the example provided in FIG. 9, a bar graph 516 provided that is generated based on application of the data cube class definition corresponding to the report (e.g., in this case "Detect Errors by Technician"). Furthermore, filtering parameters 518 may be selected to be applied (e.g., as defined by the data cube class definition used to generate report) to further filter the data presented in the graph 516. In this regard, as may be appreciated, the report displayed in the data analytics report display screen 36 may be dynamic in that the user may select various parameters to dynamically alter the presentation of the report real time. Other examples of reports that may be presented in the data analytics report display screen 36 may include charts, graphs, pivot tables (e.g., the axes of which may be selectable by a user in real time utilizing the data analytics tool), dashboards, or other data analytics tools. Furthermore, the ability to view and/or modify these various parameters associated with the report may be at least partially based upon an assigned role or resource privilege granted to a user during the authentication process for the user.

As described briefly above, the reports that may be delivered for display in a data analytics report display screen 36 may be at least partially derived upon application of a data cube class definition to data at the central server 12. A data cube class definition may be used to create a data cube for use in generation of the report. A data cube is a multidimensional data structure used to aggregate data from the associated underlying data table(s) and/or data source(s). While the term "cube" is utilized, a data cube may include more than three dimensions. As such, use of the term "cube" does not restrict a data cube to three data dimensions. Rather, a data cube may have dimensions that may correspond to associated fields in a database table of the source of the data (e.g., including any of the fields described above in relation to the dose order data), which may include many more than three dimensions. Dimensions may also be provided with levels, which may be hierarchical (e.g., to provide drilldown functionality in resulting reports based on a data cube). A data cube also may have measures comprising data elements that are values based on underlying data (e.g., that result from application of a function to the data). For example, measures such as an average, a sum, a minimum, a maximum, or other function may be applied to generate a measure included in a data cube. In this regard, the measures may be provided in the underlying data source or may be calculated based on the data in the underlying data source.

A data cube class definition may be developed to develop specific measures, dimensions, levels, values, indices, or other tools used in the data analytics process. Once all of the measures, dimensions, values, indices, etc., are defined for a data cube in the data cube class definition, and then the cube must be compiled. Compilation creates all of the necessary classes required to define and access the data in the form of the data cube. The final step is to build the data cube. The step of building the data cube populates all of the cube dimensions with data so that it can be viewed and reported on. In this regard, a batch job may, on a periodic basis, execute to synchronize the data from the source tables (e.g., the data stored at the central server 12) to the data cube as defined by the data cube class definition.

Once built, the data cube may be static, yet used by a user to generate dynamic reports (e.g., tables, charts, graphs, pivot tables, dashboards, etc.) based on the underlying data cube. The data analytics tool may have various levels of responsibility that may be used to perform various functions relative to the data analytics tools. For instance, a user may be authorized to utilize an architect tool that allows data cube class definitions to be created. Additionally, a user may be authorized to utilize an analyzer tool that allows for creation of reports, pivot tables, or other analysis tools based on a built data cube. Furthermore, a user may be allowed to utilize a viewing tool that displays results from pre-defined reports, pivot tables, dashboards, or other predefined analytics report outputs (e.g., designed by the analyzer tool). An administrator level of access may be provided that facilitates access to all levels, and other specific roles may be developed with privileges related to a plurality, but potentially less than all, responsibility levels of the data analytics tool.

Figure 4:
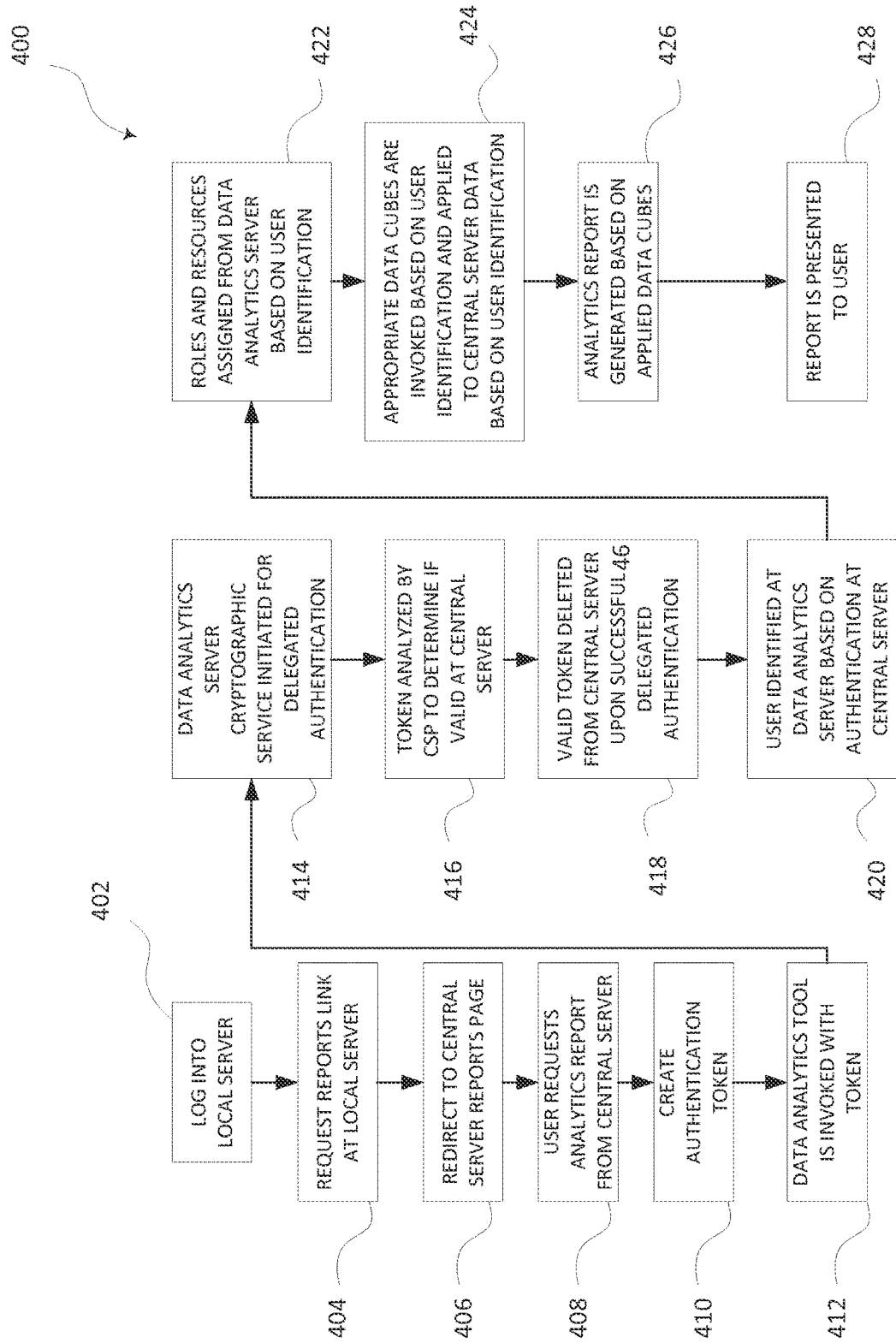
FIG. 4 is a flowchart depicting an embodiment of delegated user authentication for use in a system for data analytics.

With further reference to FIG. 4, a delegated authentication process 400 may be utilized by the system 10. The delegated authentication process 400 is shown in the form of a flowchart in FIG. 4. The delegated authentication process 400 may allow for an authenticated user that has provided sufficient credentials to access the central server 12 to be authenticated in a delegated fashion such that the analytics server 16 provides a data analytics tool relative to data stored in central server 12 upon the delegated authentication by the central server 12. The process 400 may initiate with a user logging onto a local server 402. As described above, the logging onto the local server 402 may include providing a username and password. In turn, the local server may include a database of valid username and password combinations to determine whether a user is authorized to access the local server. Upon successfully logging into the local server 402, the user may be presented with an option to request 404 access to a reports tool at the local server. Upon requesting 404 access to the reports tool at the local server, the user may be redirected 406 to the central server reports page. In this regard, the central server may provide a webpage that is displayed to the user.

The central server reports page may include a link to an analytics report if the user has sufficient credentials to access the analytics report and/or if the central server reports page is configured for the site from which the user is accessing the central server. Upon the user requesting 408 an analytics report from the central server, the central server may create 410 an authentication token that is in turn stored in a database at the central server. The central server may also invoke 412 a data analytics tool. When the data analytics tools invoke 412, the token that is created 410 may be passed to the data analytics server when the data analytics tool is invoked 412.

In this regard, when the data analytics server receives request to access a data analytics tool provided on the data analytics server, the data analytics server may initiate 414 a cryptographic service provider to perform the delegated authentication of the user requesting access to the data analytics tool. Specifically, the cryptographic service may contact the central server with the information regarding the token that is received from a user access request. If the token matches a token provided in the database at the central server, the user may be authenticated. In turn, the valid token is deleted 418 from the central server to prevent unauthorized future use of that particular token. In this regard, upon a user requesting 408 access to the analytics report from the central server, a token is created 410 and stored at the central server. The user may be redirected to invoke 412 the data analytics tool and the corresponding token created may be provided along with the request. In this regard, when the data analytics server receives a request for authentication, the cryptographic service provider may contact the central server to determine whether the token provided in the request matches one created in the database. In this regard, unauthorized requests for access to the data analytics server using a token that does not have a corresponding token stored in the central server may not be authenticated, thus reducing the ability for the tool to be accessed by unauthorized users with fraudulent or expired tokens. In this regard, the token may be analyzed by the cryptographic service provider to determine 416 if the requested user access is authenticated. In turn, the user may be identified 420 at the data analytics server at least in part based on the authentication from the central server. That is, the login information provided to the local server 402 may be in turn pass to the central server.

Additionally, the central server may provide the user information to the data analytics server 420 to identify the user. This information may comprise a session variable that may, for example, identify the user as described below and/or include information regarding a role and/or resources available to the user based on the user's credentials. This may include defining a user and or facility attempted to access the data analytics server. In turn, based on the user identification, roles and resources may be assigned 422 from the data analytics server to the user attempting to access the data analytics server to invoke a data analytics tool. In this regard, appropriate data cubes may be invoked 424 based on the user identification that are in turn applied to the central server data based on the user identification. As described above, the appropriate data cubes may filter data at the central server such that a user from a given facility may only access the data corresponding to that facility when utilizing the data analytics tool. Furthermore, depending upon the roles and resources assigned at 422, different ones of the data cubes may be provided to the user to run various different reports regarding a data. In turn, an analytics report may be generated 426 based on the plight data cubes and report may presented 428 the user.

Specifically, upon identification of the user requesting access the data analytics tool provided on the data analytics server, the authentication may include logging a user into to a data analytics environment as a data analytics user with the appropriate roles assigned. For instance, during delegated authentication, the requesting user may be logged-in with a user name in the format <customerID>|<userID>|<username>, where <customerid> is the customer ID (e.g., corresponding to a facility) from which the user is accessing the central report pages. For example, the user identification may be provided as part of a session variable communicated to the data analytics server. Rather than the customer ID, a 0 may be used to populate this field for support users accessing the data analytics will from the central server directly, <userID> may be the user ID corresponding to the user (e.g., with 0 being used again for support users accessing the data analytics tool directly from the central server), and the username may be the user's login id. As an example, the Administrator user from customer ID 5, with a central server user id of 10 will be logged in as "5|10|Administrator".

In turn, when accessing data for generation of reports using the data analytics tool, the user identification (e.g., such as that described above) may be utilized to limit the data to which a data cube class definition is applied or limit the data to which a user may access when generating a report. For instance, in one implementation, a base cube class definition may be provided from which all other data cube class definitions dependent. In this regard, all data cube class definitions may inherit from the base cube class definition. To prevent unauthorized access from the local server, all developed data analytics tool data cube class definitions inherit from the base cube class definition that comprises a special security filter class definition. In this regard, the base queue class definition may include an organization identifier and a customer identifier as default dimensions, in addition to any other dimensions to be included in the cube definition. The base cube class definition may use these two properties to include only records from the specific customer or organization account based upon the received user identification information during the user authentication process. This acts as a security mechanism to prevent users from accessing other customer data on the central server.

For instance, to filter central server data based on a user's access to organization or site data, the base cube detects whether the user is an organization level user or a site level user. Based on the evaluation, a multidimensional expression filter string is assembled based on either the organization or sites that the user belongs to. Once the filter string is assembled, the multidimensional expression filter is applied to all data in the base cube (e.g., which must include dimensions corresponding to the organization ID or client ID) and limits the information that the user sees in any report. As such, the base cube class definition may, in conjunction with the user identification information received during the authentication process, serve to limit access for a user to data only corresponding to the facility (or organization) to which the user belongs or from which the user is accessing the tool. As such, while the data analytics tool operates on aggregated data corresponding to a plurality of facilities, the base cube class definition from which all other data cube class definitions depend, may serve to limit access to data correspond to the user's facility.

Because internal users (e.g., users accessing the data analytics tool from the central server directly) must also be able to access the data from the data analytics tool, the base cube class definition also detects whether or not the user has accessed the environment from the local server or directly using the central server. It may accomplish this by determining if the session variables for a given user session in which a user requests access to the data analytics tool is populated with the expected parameters. If so, then access is assumed to by via the local server. If not, then access is assumed to by via the central server screens and a check is made of the roles attributed to the user session definition to see if the correct roles are assigned to the user accessing the data analytics tool from the central server.

Additionally, a protected heath information (PHI) parameter may be used to indicate if PHI information is exposed by the cube. This will allow reports to be generated to identify cubes with PHI information. Cubes containing PHI information may also require a specific resource attributable to specific users to access the cube. This will limit access to pivot tables and dashboards derived from those cubes containing PHI. In this regard, a particular concern regarding exchange of medical information includes maintaining the privacy of patients as it relates to the exchange of medical information. For instance, medical information may include patient identifying information (e.g., potentially including PHI). In this regard, dissemination of medical information may subject to restrictions due to regulatory issues (e.g., the Health Insurance Portability and Accountability Act (HIPAA) in the United States) may prohibit dissemination of medical information with PHI or other privacy concerns. While HIPAA may define PHI, it may be appreciated that as used herein PHI may include data included in the HIPAA definition as well as other data. For instance, any patient identifying information (e.g., patient name, patient identification number, etc.) may be defined as PHI.

Furthermore, data cube class definitions may include data transformations that are applied to data from the data source. These transformations may include generating calculated measures based on underlying source data. The transformations may also include modification to the source data. For example, in one specific example related to total parenteral nutrition (TPN) doses, certain dose order record fields may be acted upon by a corresponding data cube class definition. In this regard, a data cube class definition, during the build process, may replace a given dose order field (e.g., a DoseDescription field) with the value from another field (e.g., the DoseDrugNames field). This transformation may be applied only to a certain type of doses (e.g., for TPN doses as determined by a record flag indicating whether the dose order is a TPN order or based on a drug contained in the order). As such, during cube building, a record from the source data table will be determined if the record contains the appropriate fields (e.g., "DoseDescription", "TPN", and "DoseDrugNames" following the example above). Once a record is determined to be a TPN order to which the data transformation applies, the data analytics server will check the TPN field and if it is set to 1 (the dose is TPN) then the value of field "DoseDrugNames" may be copied into the field "DoseDescription".

Additionally, each data cube class definition is such that when building the data, the cube will not load any records from sites designated with the "Data Exclusion" flag. In this regard, the base cube class definition may determine if a record is for a customer site with the data exclusion designation and if so, it will skip the record from being loaded. The data exclusion designation 522 is set in the server detail page 520 shown in FIG. 10.

Figure 10:
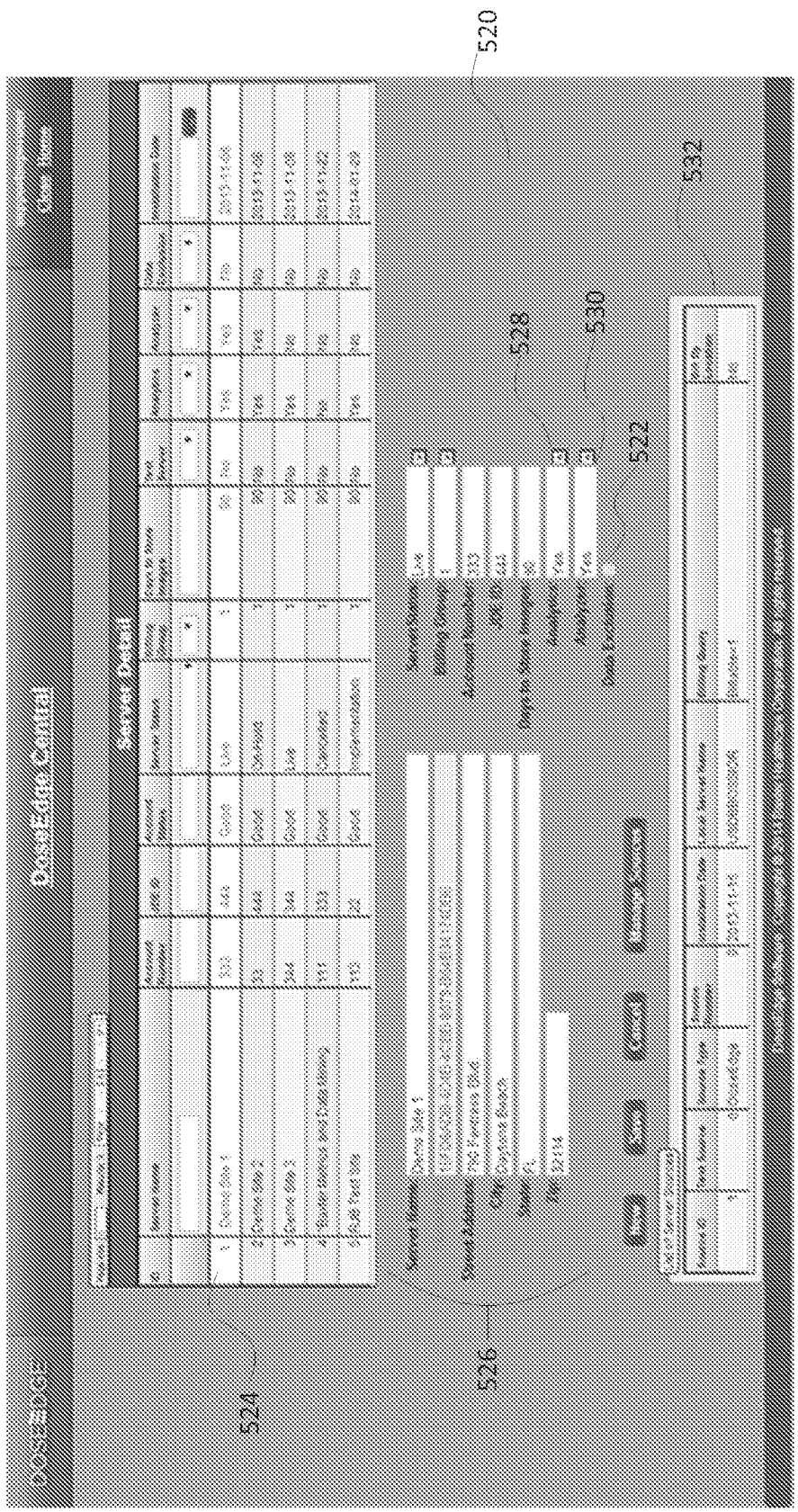
FIG. 10 depicts an embodiment of a data analytics tool configuration setup.

In this regard and with further reference to FIG. 10, a server detail page 520 is shown that allows for configuration of behavior of the data analytics tool when accessed by various servers. In this regard, a listing 524 of local servers is provided that may provide users access to the data analytics tool. For each server in the listing 524, a server configuration field 526 is provided. In this field 526, details regarding the server (e.g., location address, server status, billing information, account number, server configuration details, etc.) may be configured. Specifically, an analytics access selection field 528 may allow an administrator to set permissions related users from a given local server having access to the data analytics tool (e.g., thus determining whether a link 506 to the data analytics tool is provided on the central reports screen 32 of FIG. 7. Furthermore, an analytics analyzer selection field 530 may be provided that is used to set permissions related users from a given local server having access to an analyzer of the data analytics tool (e.g., where reports, dashboards, pivot tables, or the like may be generated). Additionally, a data source listing 532 may be provided in relation to each particular data source of a given server in the listing 524.

With returned reference to data cube class definitions, certain useful data transformation techniques may be provided for use with a data cube class definition. For instance, a protected health information (PHI) parameter may be provided (e.g., with all cubes) to identify if the cube exposes PHI information. If a parameter indicative of PHI being present is determined to be true, then the cube contains PHI fields, otherwise the cube is not considered to contain PHI fields. The PHI parameter may be dynamically generated based on the underlying data source to which the cube class definition is applied (e.g., whether any source data is determined to have PHI).

Additionally, a delta time function may be provided. The delta time function may be used to calculate the time difference between two times. Each time value may be passed as a parameter to the function and the time difference (e.g., as measured in minutes, hours, days, seconds, etc.) is returned as the value of the dimension. As such, when a cube measure is created that will use the time function, a measure name may also created that is representative of the time measure being extracted. For instance, a measure called "DeliveredTimeMinutes" could be defined as the difference between the time the dose was delivered to the patient and the time it was received in the pharmacy. Continuing the example, the data cube class definition having the cube measure "DeliveredTimeMinutes" may have instructions such that a specific method call performs the actual calculation and the source data elements are the time values to be compared. For instance, the specific method call may return the difference of the defined time measures to be compared and return the value as a positive integer.

Furthermore, one or more custom time functions may be created. Custom functions can be created to evaluate any number of desired results. For a custom time reporting function that relies on multiple inputs to evaluate an elapsed time, a custom time function that may take four time inputs and evaluates the dose preparation time based on coded criteria using the four input values may be provided. This method may take the four defined time value and perform specific calculations thereto (e.g., evaluating the time doses were at various stages of processing defined by the four inputs).

Additionally, record filtering may be provided by a data cube class definition. This may allow for record filtering to eliminate records from the cube dataset that are not needed. This may be thought of as similar to adding a WHERE clause to and SQL statement. In this regard, by setting up an "if" statement to determine if a record should be included or not records can be excluded from the fact table when building the cube. For instance, in an example a data cube class definition may filter records based on the contents of one or more given dimensions in the cube (e.g., Type and ErrorCategory).

Additionally, the cube definition may include the listing tag which defines the fields to display to the users when they drill-down within a pivot table or dashboard. A pivot table may have multiple listings defined. When defining a pivot table based on a cube, the pivot table designer may select which listing to display when the end-user drills down on the pivot table. The dashboards based on that pivot table may also inherit the ability to drill down in the data to display the listing specified during the pivot table design.

Furthermore, a data cube class definition may include an operation that is utilized to de-identify patient information contained within the data for a given data cube. For example, a hash function or the like may be applied to the patient information, thereby rendering the resulting data in the data cube non-identifying of the patient. In further embodiments, the source data for a data cube class definition may be a data source in which the patient identifying information has been removed (e.g. by a hash function or the like).

Additionally, upon a user accessing the data analytics tool, a log event may be created that provide logging information with respect to the user accessing the data analytics tool and various specific resources accessed during a session. In this regard, log entries for a given user session and/or navigation occurring within the user session may be generated (e.g., by a logging module at the central server 12 and/or data analytics server 16). These log sessions may provide access regarding a particular session to achieve user is defined and may provide details regarding specific navigation of the user during the session. In turn, the user logs may be reviewed to determine which users access is accessed which resources and particular parameters in connection with that access. In connection therewith, a schema 600 corresponding to an embodiment of a user log is depicted in FIG. 11.

Figure 11:
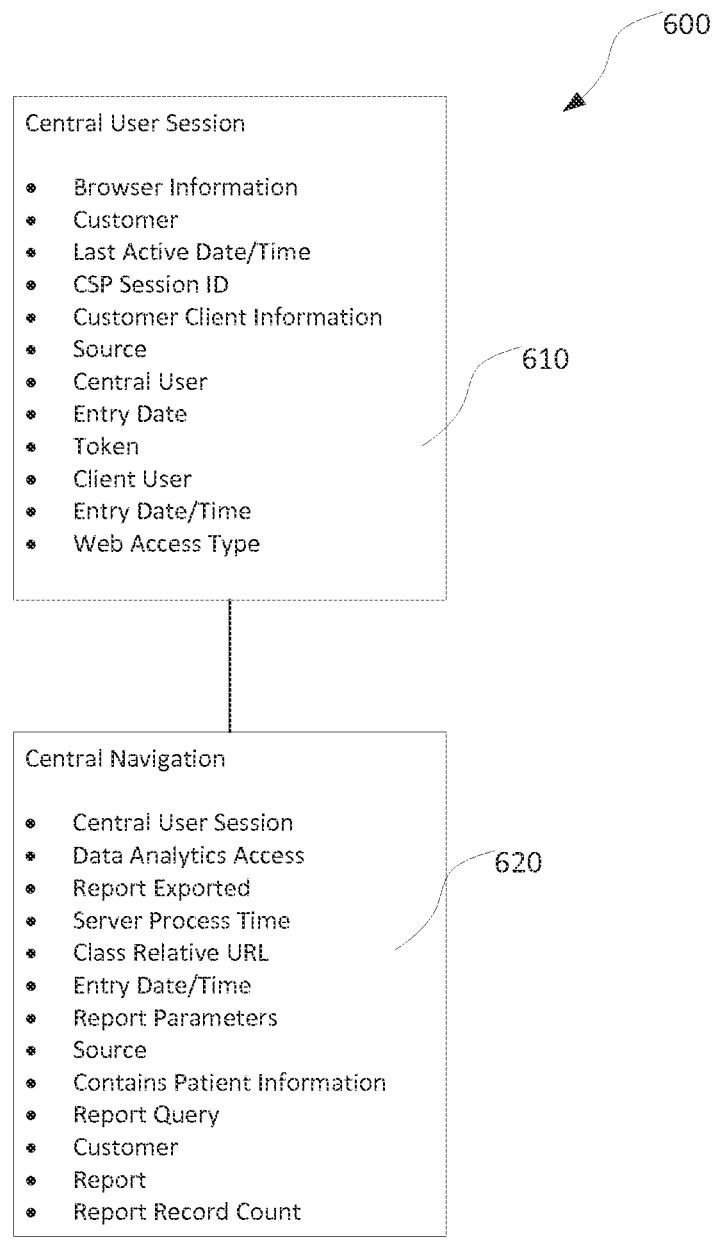
FIG. 11 depicts an embodiment of a logging schema that may be used in connection with a data analytics tool.

Accordingly, with further reference to FIG. 11, the schema 600 used to generate log records may include a central user session log 610 created for each session by a user. Sub-records in the form of central navigation log 620 may be created for each central user session log 610 that tracks specific navigation of the user during the session corresponding to the central user session log 610. In this regard, a session log record may be generated according to the schema for the central user session log 610. Accordingly, the session log 610 may include the property "Browser Information" as a string that stores the browser used by the user. The session log 610 may also include a property "CSP Session ID" that corresponds to a reference to the cryptographic service provider session identifier used to serve the user session being logged (e.g., potentially corresponding to the token received from the user). The log 610 may also include the property "Central User" that links to the user related to this session. This may indicate a central user accessing the tool directly from the central server as a support user from central server if applicable. The log 610 may also include a property "Client User" that comprises a link to the user related to this session from the client application. The log 610 may also include a property "Customer" that includes the identity of the customer from which the user is accessing the tool. The log 610 may also include the property "Customer Client Information" that may include the site statistics to get specific details about the client from which the user is accessing the tool. The log 610 may also include the property Entry Date that indicates the date the session was entered. The log 610 may also include the property "Entry Date Time" that comprises the date/time the session was entered. The log 610 may also include the property "Last Active Date Time" that corresponds to the date/time the session was last active or updated. The log 610 may include the property "Source" that provides information regarding the customer source if the user was redirected from a local server. The log 610 may also include the property "Token" as that corresponds to the uniquely identifiable token described above. Furthermore, the log 610 may include the property "Web Access Type" that comprises an identity of the specific application of the data analytics tool that was accessed.

Additionally, for each session log, sub-records comprising a central navigation log 620 corresponding to session activity or navigation may be created. The central navigation log 620 may include properties such as, for example, the property "Central User Session" that links to the central user session log 610 associated with the navigation being logged. The log 620 may also include the property "Class Relative URL" corresponding to the class accessed. The property "Contains Patient Information" may be a true/false indication as to whether the resource (e.g., page, report, tool) being accessed contains PHI information. In this regard, either the a parameter "HASPHI" may be set to 1, or the report definition field "ContainsPHI" may be set to 1 if a report is being executed that includes PHI. The log 620 may also include the property "Customer" that indicates the customer from which the user is accessing the tool. The property "Data Analytics Access" may indicate the resources from the data analytics tool utilized (e.g., including the data cube definitions invoked or the like). The property "Entry Date" may correspond to the date the session was entered, and the property "Entry Date Time" may correspond to the date/time the session was entered. The log 620 may also include the property "Report" that indicates the identity of a report accessed, if any. The property "Report Exported" may include an indicator as to whether the report was exported. The property "Report Parameters" may include the parameters selected by the user when running a report or otherwise utilizing the data analytics tool. The property "Report Query" may include an identity of the query executed to generate a report, and "Report Record Count" may include the record returned by the report. The property "Server Process Time" may correspond to the processing time in ms (milliseconds). The property "Source" may include an indication of the customer source if the user was redirected from a local server.

In relation to the foregoing description, it may be appreciated that the data analytics tool described herein may be utilized in a number of different contexts in relation to dose order data. Thus, while dose order data is referenced throughout the present disclosure, such data may include and/or provide for far reaching data analytics. For instance, as described above the dose order data upon which the data analytics tool may be invoked may include a plurality of different dose order data classes that may include information related to the dose order, the preparation of the dose order, products used during the preparation of the dose order, or any other related information. In this regard, it may be appreciated that a plurality of different categories of data cube class definitions may be provided in a data analytics tool. Importantly, all such data cube class definitions may depend from the base cube class definition that permits selective, secure access to the facility (or organization) specific data corresponding to a given user.

For instance, a number of categories of data cube class definitions may be provided. For example, the data cube class definitions may relate to, as way of example, general pharmacy workflow activity, pharmacy performance metrics, pharmacy exceptions, pharmacy usage and waste, data related to products and therapies, compliance data, and user logs. In this regard, examples of data cube class definitions in the general pharmacy workflow activity category may include a data cube class definition corresponding to basic statistics regarding dose orders, dose order items, dose preparation information, dose claim activities, dose scan events, dose verification history, and procedure summaries. In this regard, the data cube class definition corresponding to basic dose statistics may include dose dimensions related to, for example, dose administration time, whether the dose was a first dose in a series of doses, the dose route (e.g., intravenous, oral, intramuscular, etc.), whether the dose a hazmat dose, whether the dose is a high-risk doses, the nursing unit corresponding to the dose, whether the dose is a STAT dose, whether the dose is a total parenteral nutrition (TPN) dose, the type of TPN dose, whether the dose includes an unknown drug, the technician that prepared the dose, the workstation that was used to prepare the dose, whether the dose is a stock dose, whether the dose is a dilution dose, the dose status, the dose preparation date, the dose entry hour, and the dose entry minute. Furthermore, any of the foregoing dimensions may include normalized versions of the dimensions (e.g. for instance in the case of normalized drug names, normalized amounts, normalized units, or the like). Furthermore, some data cube class definitions that provide dose order summary data may include measures related to the total volume of the dose, the final volume of the dose, a QS volume of the dose, a QS diluent name, a stock dose count, a dilution dose count, a number of rework doses, in-line verification of a dose, the number of images per prepared dose, the number of fully compounded doses by a compounder, the number of dose manual additions, the number of doses with material requests, the number of doses having expanded drug names, the number of doses by status, the number doses by route, the number of attachments for a dose order record, and a normalized dose description. For data cube class definitions regarding dose order items, the data cube class definitions may relate to dimensions corresponding to the dose status (e.g., to filter our records that have not actually been delivered to a patient), a dose description, a dose description normalized based on formulary drug names, base units, and diluents, whether the dose is a stock dose, whether the dose is a dilution dose, whether the dose is a hazmat dose, whether the dose is a high risk dose, the total volume of the dose (e.g., including contributions small products), the final volume of the dose (e.g., as specified for the dose order by an electronic medical record (EMR) system or hospital information system (HIS)), the QS volume, and a QS diluent name Data cube class definitions related to the dose preparation information may include data dimensions corresponding to the preparation mode used to prepare a dose, preparation mode options the time the dose was prepared, and a calculated QS volume for a dose. Data cube class definitions may relate to the occurrence of a pharmacist claiming a dose during verification (e.g., from another use who has a session verifying the dose). In this regard, dose claim data cube class definitions may include data dimensions corresponding to whether a dose was claimed during verification, whether the individual claiming the dose disposed of the dose that was claimed, the reason a claim was successful or unsuccessful, whether the claim was overwriting another user's claim, the time a claim is active, the overwriting user, the overridden user, and a dose identifier. Data cube class definitions related to dose scan events may include data dimensions related to the scan event name, the dose order identifier, the product lot identifier, a catalog identifier, a user identifier for the scan, and the event target (e.g., calculated to determine the dose order, product blog, or kit event type). Data cube class definitions related to dose verification history may include data dimensions corresponding to the user identifier of the user who verifies the dose, the date/time the dose is verified, the results of the verification, the reason provided during verification (e.g., for requeue, cancellation, and rework orders), the dose identifier, the verification type, the disposition of the dose, a reason for remake, and a rejected product log. Data cube class definitions related to procedure records may include the entry date and time of the dose, the completed date and time of the dose, the user identifier of the technician used to prepare the dose, the workstation identifier of the workstation used to prepare the dose, the name of the dose, a central formulary procedure ID (e.g., corresponding to a procedure presented the user in the preparation), a procedure type, a completed action count, a required action count, a total action count, and a completion time.

Additionally, a number of performance data cube class definitions may be provided that may include information regarding dose turnaround time and system performance. For data cube class definitions regarding dose turnaround time, the data cube may include dimensions related to a workstation used to prepare the dose, a preparation location name, a technician name, a patient location, a nursing unit corresponding to the dose, a priority of the dose, whether the dose is a STAT dose, whether the dose is a hazmat dose, a number of items in the dose, whether the dose is a stock order, dose drug names, and a preparation date/time. Furthermore, a number of measures may provided for a data cube class definition related to the dose turnaround time including an average time preparation, a delivered time, a waiting for preparation time, a time to resume preparation after an in-line verification or rework, a time until dose distribution, a average time to verify the dose, and an average time to sort the dose. The data cube class definition regarding system performance may include data dimensions corresponding to the time/date of a log, the calculated record length of the session, a function name, an average data analytics server execution time, and average client server execution time, a maximum data analytics server execution time, a maximum client server execution time, a minimum data analytics server execution time, a minimum client server execution time, and an execution count.

Furthermore, a number of data cube class definitions related to dose exceptions may be provided. Examples may include data cube class definitions related to prevented error (e.g., scan errors), detected errors, bypass reasons, dose order modifications, and alerts. Accordingly, prevented errors may correspond to errors identified by the pharmacy workflow management application automatically without human intervention (e.g., scan errors or the like) and the detected errors may include errors identified by a human interacting with the pharmacy workflow management application such as a pharmacist during a dose review. A data cube class definition related to scan errors may include data dimensions related to doses containing a prevented error generated during dose preparation, a dose category, a dose identifier, a scanned barcode, a scan formulary product information, scan product log information, technician information, and workstation information. The data cube class definition related detected errors may include detected error data generated at the pharmacist check station. Data dimensions contained within the detected errors data cube class definition may include a reason for remaking a dose, pharmacist information, technician information, workstation information, preparation location, a nursing unit associated with the dose, a dose route for the dose, whether the dose is a hazmat dose, a type of hazmat dose, whether the dose is a TPN order, a the dose description. A data cube class definition related to bypass reasons may include information related to doses in connection with a bypass print operation whereby the dose order, upon being received by the pharmacy workflow management application, is bypassed for printing of the dose order by a label printer in a traditional fashion. As such, data dimension for the bypass reasons data cube class definition may include an indication that the dose was bypassed, a time and date of the order entry, drug information corresponding to the dose order, information regarding the source of the data order, etc. A data queue class definition regarding dose order modifications may include data dimensions including what modification was made to the dose including an administration date/time update, a discontinuation of a dose, a change in priority for dose, a movement of the dose onto or off of a hold status, an expiration date/time of a dose due to using a stock product with an earlier expiration date, whether an adjustment was done automatically by the system or intentionally by user, who made a modification, and why a modification was necessary (e.g., if the site is configured to enter reason for modification). A data cube class definition related to dose alerts may include data dimensions corresponding to whether a dose is subject to an alert during the preparation process and other dose identifying information that may allow trends with relation to a dose alert to be determined. Other data cube class definitions may include data dimensions regarding received alerts (e.g., from within a pharmacy workflow management system or from an external alert provider) regarding dose orders, patients, drugs, or some other portion of data stored by a pharmacy workflow management application.

Data cube class definitions may also relate to usage and waste metrics in the pharmacy. Examples may include data cube class definitions related to product waste, drug waste, and products siblings. Accordingly, a product waste data cube class definition may include data dimensions corresponding to data from unused/expired products such as product preparation location, preparing technician information, dose status, dose name, an NDC code for drugs in the dose, a total volume of the dose, a current volume of the dose, an expiration date of the dose, a number of prepared doses, an unused volume ratio (i.e., the current volume divided by the total volume), a cost for the dose (e.g., referenced from a formulary record for a drug or product associated with the dose), and whether the dose was a multi-use dose. For instance, a resulting report based on the product waste data cube generated from the product waste class definition may include an aggregate of an amount of drug wasted over a given time period and/or the cost associated with that corresponding waste (e.g., using underlying data and/or measures defined in the data cube class definition). A drug waste data cube class definition may include data dimensions corresponding to a product log identifier, an entry date, an expiration date, an activation date, a number of beyond use hours for the dose, a drug name, an amount of the dose, units of the dose, whether the dose is a hazmat dose, whether the dose is a high risk dose, and whether the dose of the diluent dose. In this regard, the beyond use hours data dimension may be a calculated measure that includes the difference between the expiration date and activation date and hours.

The product and therapy category of the data cube class definitions may include data cube class definitions related to therapy summaries and drug combinations. Accordingly, a data queue class definition related to therapy summaries may include data dimensions corresponding to the ability to see a drug therapy instance in terms of average duration (e.g., a number of days, number of doses, or total dose amounts) including, for example, a customer identifier, a source identifier, an entry date for the dose, drug names for the dose, a dose description, and a therapy ID. The drug combination data cube class definition may include a "crosstab" showing the frequency of a combination of drugs when given together. Data dimensions for this data cube class definition may include a customer identifier, a source identifier, an entry date for the dose, a drug name associated with the dose, an amount of the dose, a unit of the dose, and a dose identifier.

A number of data cube class definitions may be related to compliance tracking. Examples may include data cube class definitions related to schedule task histories and weight measurements. The schedule task histories data cube class definition may include data dimensions that may allow for compliance tracking with scheduled tasks to be completed in relation to workstations. In this regard, the data dimensions for the data cube may include workstation tasks, a missed task dose count (e.g., including the number of bad doses because a clean task is not completed on time), information on completed tasks (e.g., including the user, time, workstation, whether the task was overdue, and an overdue time), how many doses were prepared on an overdue workstation by user, a frequency type, a frequency value, a previous completion date/time, a previous due date time, and next due date time. A weight measurement data cube class definition may include data corresponding to weight measurements recorded dose preparation workstation. Furthermore, data queue class definitions related to compliance tracking may allow for filtering and/or searching of doses based on a number of different data dimensions such as, for example, dose type, dose preparation date, technician, location, or any other appropriate dimension. Furthermore, the dynamic report generated based on the compliance tracking may allow for a user to drill down through various dimension levels. At a given level, user may select to view individual dose order records comprising a given set of data (e.g., a chart cell or graph portion may correspond to a certain number of doses, which may be revealed as a listing of the specific dose order records referenced by the chart cell a graph portion upon selection by the user). That is, the report may allow a user to define or select various parameters that allow a user to access a list of doses that meet a criteria established by the user using the selection of various parameters. The compliance tracking data cube may include a link that allows a user to retrieve a dose order log corresponding to a given dose order contained in the listing of specific dose order records. The dose order log may include any or all information related to the selected dose order (e.g., including data regarding the dose order record outside of the data dimensions of the data cube used to filter or search for the dose order itself). That is, the dose order log may include any or all information regarding the dose order log even if that dose order information does not comprise a dimension contained in the data cube used to obtain the link to access the dose order log for the dose order record. In an application, the dose order log linked to in the compliance tracking data cube may correspond to a dose order log with a specific format and/or data content dictated by an authority such as a government regulatory body or the like for use in determining regulatory compliance.

Additionally, a number of data cube class definitions may be related to user logs. Examples may include data related web sessions, data related to workstation sessions, data related to central user sessions, and data related to central user navigation, and audit logs. A data queue class definition for web sessions information may include data dimensions corresponding to information relevant to web-based user sessions including, for example, an IP address of the user, a login date/time, a logout date/time, a browser name, a browser version, a browser extension installation version, a length of the session, a indication of the breakdown between site configuration time and dose preparation functionality time, an average response time from the server for web service calls, and an average response time for webpage requests. The data cube class definition related to workstation sessions may include data dimensions related to a login date/time for workstation, a logout date/time for the workstation, a workstation software version, the workstation name, a work station location, a username accessing the workstation, and a last activity date/time. A data cube class definition related to central user sessions may include data dimensions corresponding to a central session log, a total session time, and a browser type/version. A queue class definitions related to central user navigation may be based on a central navigation log. An audit log data class definition may be operative to compare a full snapshot of audit logs and identify which fields have changed.

Other data cube class definitions may be provided without limitation that may leverage various ones of the data dimensions present in dose order information. Furthermore, the source data to which data cube class definitions may extend beyond dose order data. For instance, additional data sources (e.g., located at hospital information systems, pharmacy information systems, laboratories, surgical data repositories, formulary records, national healthcare databases, etc.) may be accessible by the data analytics tool. In this regard, data cube class definitions that reference such data sources may be provided. Additionally, data cube class definitions may be provided for use in building data cubes that reference multiple data sources (e.g., including dose order data as well as other data sources such as those listed above including hospital information systems, pharmacy information systems, laboratories, surgical data repositories, and national healthcare databases). In any regard, the foregoing data cube class definitions may be utilized in building corresponding data cubes. In this regard, one or more reports may be generated that reference a data cube for presentation of data to a user. The reports may take the form of pivot tables, dashboards, charts, graphs, or other report mechanisms. The reports may be filterable based on various different data dimensions such as, for example, dose order types, dates, dose statuses, technician, pharmacist, or any other data dimension included in the data cube and defined relative to the report (e.g., which may be modifiable by a user with appropriate role or responsibility). Furthermore, the reports may include drill downs based on the dimension levels as discussed above to provide increasingly detailed data based on a subset of data for a given dimension. In this regard, a user may be able to utilize the reports to identify trends, anomalies, patterns, or other information from the data presented in the dynamic report generated based on a data cube.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A method for providing a user selective access to a data analytics tool for processing a multidimensional data set corresponding to dose order records for use in providing data analytics to the user regarding a subset of the dose order records of the multidimensional data set, the method comprising:
    storing a multidimensional data set comprising information corresponding to a plurality of dose order records, wherein the plurality of dose order records of the multidimensional data set comprises at least one indication of a facility corresponding to the dose order records, and wherein the multidimensional data set comprises dose order records corresponding to a plurality of facilities;
    receiving user information from a user at one of the plurality of facilities, wherein the user information is indicative of a given facility from which the user is accessing a data analytics tool;
    providing the data analytics tool access to the multidimensional data set to generate a dynamically generated report regarding a subset of the multidimensional data set corresponding to the given facility from which the user is accessing the data analytics tool; and
    presenting to the user at a user interface the dynamically generated report regarding the subset of the multidimensional data set corresponding to the given facility from which the user is accessing the data analytics tool.

2. The method of claim 1, wherein the data analytics tool comprises a plurality of data cube class definitions applicable to the multidimensional data set to generate the dynamically generated report.

3. The method of claim 2, wherein the plurality of data cube class definitions comprises a base cube class definition from which all others of the plurality of data cube class definitions depend.

4. The method of claim 3, wherein the base cube class definition includes at least one data dimension related to the at least one indication of a facility corresponding to the dose order records.

5. The method of claim 4, further comprising:
applying the base cube class definition to the multidimensional data set based on the user information indicative of the given facility from which the user is accessing the data analytics tool; and
building a data cube based on the applying that limits data accessible by the user to the subset of the multidimensional data set corresponding to the given facility from which the user is accessing the data analytics tool.

6. The method of claim 5, wherein the building further comprises:
performing at least one data transformation operation on the subset of the multidimensional data set, wherein the at least one data transformation operation is defined in the base cube class definition.

7. The method of claim 6, wherein the at least one data transformation operation comprises automatically transcribing a first data field for each given dose order record in the subset with a second data field of the respective ones of the dose order records of the subset.

8. The method of claim 7, wherein the at least one data transformation operation is applied only to a given type of the dose order records.

9. The method of claim 8, wherein the given type of the dose order records includes total parenteral nutrition (TPN) doses, the first data field comprises a dose description field, and the second data field comprises a drug name field for the given dose.

10. The method of claim 5, further comprising:
invoking another of the data cube class definitions depending from the base cube class definition for application to the subset of the multidimensional data set corresponding to the given facility from which the user is accessing the data analytics tool to generate the dynamically generated report regarding the subset of the multidimensional data set.

11. The method of claim 3, wherein the plurality of data cube class definitions includes a parameter indicative of whether data cubes built using the data cube class definitions include protected health information (PHI).

12. The method of claim 11, wherein the parameter is dynamically generated based on at least one dimension of the data cube class definition.

13. The method of claim 1, wherein the receiving further comprises:
receiving login information at a local server resident at the facility from which the user is accessing the data analytics tool to initiate a user session;
authenticating the user to a central server based on the login information received at the local server; and
populating a session variable related to the user session based on authenticated user login information,
wherein the session variable comprises the user information indicative of the given facility from which the user is accessing the data analytics tool.

14. The method of claim 13, further comprising:
passing a token at least partially based on the session variable to the data analytics tool, wherein the token is compared to available tokens at the central server to determine if the user is to be granted access to the data analytics tool.

15. The method of claim 14, wherein upon matching the token to one of the available tokens, the token is issued to the user and the corresponding available token is removed from the central server.

16. The method of claim 13, wherein the session variable includes a role definition for the user generated based at least in part on the login information received.

17. The method of claim 16, wherein the role definition includes indications as to an ability of the user in relation to viewing reports, editing reports, viewing cube class definitions, editing cube class definitions, viewing pivot tables, editing pivot tables, viewing dashboards, and editing dashboards.

18. The method of claim 1, further comprising:
logging user activity in relation to the use of the data analytics tool by the user.

19. The method of claim 18, wherein the logging comprises recording information regarding the user and the usage of the data analytics tool by the user.

20. The method of claim 19, wherein the logging comprises recording the identity of the dynamically generated report presented to the user.

21. The method of claim 20, wherein the logging comprises recording whether the dynamically generated report presented to the user contained protected health information (PHI).

22. The method of claim 1, wherein the multidimensional data set comprises data regarding an identity of doses corresponding to the plurality of dose order records, data regarding steps for preparing the doses, data regarding a timing of the doses, data regarding errors that occurred during dose preparation of the doses, data regarding product waste, data regarding drug usage, data regarding drug therapies administered, data regarding drug interactions, and data corresponding to alerts at a pharmacy workflow management application.

* * * * *